United States Patent [19]

Gilheany et al.

[11] Patent Number: 5,126,494
[45] Date of Patent: Jun. 30, 1992

[54] METHODS FOR CATALYTIC ASYMMETRIC DIHYDROXYLATION OF OLEFINS

[75] Inventors: Declan Gilheany, Maynooth, Ireland; Byeong M. Kim, Cambridge, Mass.; Hoi-Lun Kwong, Somerville, Mass.; K. Barry Sharpless; Tomoyuki Shibata, both of Brookline, Mass.

[73] Assignee: Massachusetts Institute of Technology, Cambridge, Mass.

[21] Appl. No.: 512,934

[22] Filed: Apr. 23, 1990

Related U.S. Application Data

[63] Continuation-in-part of Ser. No. 250,378, Sep. 28, 1988, Pat. No. 4,965,364, which is a continuation-in-part of Ser. No. 159,068, Feb. 23, 1988, Pat. No. 4,871,855, which is a continuation-in-part of Ser. No. 142,692, Jan. 11, 1988, abandoned.

[51] Int. Cl.$^5$ .................. C07C 33/02; C07C 33/26
[52] U.S. Cl. .................. 568/807; 546/134; 568/715; 568/815; 568/833; 568/847; 568/860
[58] Field of Search .............. 568/815, 860, 833, 847, 568/852, 715, 806, 807, 811; 546/134

[56] References Cited

U.S. PATENT DOCUMENTS

| | | | |
|---|---|---|---|
| 4,482,763 | 11/1984 | Austin et al. | 568/860 |
| 4,496,778 | 1/1985 | Myers et al. | 568/860 |
| 4,496,779 | 1/1985 | Myers et al. | 568/860 |
| 4,965,364 | 10/1990 | Marko et al. | 568/811 |

FOREIGN PATENT DOCUMENTS

| | | | |
|---|---|---|---|
| 0053023 | 6/1982 | European Pat. Off. | 568/860 |
| 0077202 | 4/1983 | European Pat. Off. | 568/860 |
| 0098701 | 1/1984 | European Pat. Off. | 568/860 |
| 0101167 | 2/1984 | European Pat. Off. | 568/860 |
| WO89/02428 | 3/1989 | PCT Int'l Appl. | 568/860 |

OTHER PUBLICATIONS

E. N. Jacobsen et al., *J. American Chemical Society*, 110:1968–1970 (1988).
K. B. Sharpless and K. Akashi, *J. American Chemical Society*, 98(7):1986–1987 (1976).
K. Akashi et al., *J. Organic Chemistry*, 43(10):2063–2066 (1978).
E. Herranz and K. B. Sharpless, *J. Organic Chemistry*, 43(12): 2544–2548 (1978).
B. A. Cartwright et al., *J.C.S. Chem. Comm.*, pp. 853–854 (1978).
R. Collin et al., *Biochimica et Biophysica Acta*, 354:152–154 (1974).
V. Van Rheenen et al., *Tetrahedron Letters*, 23:1973–1976 (1976).
R. Ray and D. S. Matteson, *Tetrahedron Letters*, 21:449–450 (1980).
S. G. Hentges and K. B. Sharpless, *J. American Chemical Society*, 102(12):4263–4265 (1980).
H. S. Mosher and J. D. Morrison, *Science*, 221:1013–1019 (1983).
T. H. Maugh, *Science*, 221:351–354 (1983).
R. Criegee, *J. Liebigs. Ann. Chem.*, 522:75–96 (1936)—(Translation from German).

(List continued on next page.)

*Primary Examiner*—Werren B. Lone
*Attorney, Agent, or Firm*—Hamilton, Brook, Smith & Reynolds

[57] ABSTRACT

Osmium-catalyzed methods of addition to an olefin are discussed. In the method of asymmetric dihydroxylation of the present invention, an olefin, a chiral ligand, an organic solvent, water, an oxidant and an osmium-containing compound are combined. In the method of asymmetric oxyamination of the present invention, an olefin, a chiral ligand, an organic solvent, water, a metallo-chloramine derivative, an osmium-containing compound and, optionally, a tetraalkyl ammonium compound are combined. In the method of asymmetric diamination of the present invention, an olefin, a chiral ligand, an organic solvent, a metallo-chloramine derivative, an amine and an osmium-containing compound are combined. In one embodiment, an olefin, a chiral ligand which is a polymeric dihydroquinidine derivative or a dihydroquinine derivative, acetone, water, a base, an oxidant and osmium tetroxide are combined to effect asymmetric dihydroxylation of the olefin.

23 Claims, 4 Drawing Sheets

OTHER PUBLICATIONS

R. Iwasawa et al., *Chemistry Letters,* pp. 1721–1724 (1988).

K. B. Sharpless et al., *J. American Chemical Soc.,* 97:2305–2307 (1975).

K. B. Sharpless et al., *J. Organic Chemistry,* 41:177–179 (1975).

A. O. Chong et al., *J. American Chem. Soc.,* 99:3420–3426 (1977).

E. Herranz et al., *J. Am. Chem. Soc.,* 100:3596–3598 (1978).

M. Schroder, *Chem. Rev.,* 80:187–213 (1980).

T. Yamada and K. Narasaka, *Chem. Letters,* 131–134 (1986).

K. B. Sharpless, *Chemistry in Britain* (Jan. 1986).

M. Tokles and J. K. Snyder, *Tetrahedron Letters,* 27:3951–3954 (1986).

Y. Gao et al., *J. Am. Chem. Soc,* 109:5765–5779 (1987).

Ab. A. Smaardijk and H. Wynberg, *J. Org. Chem., 52:135–137 (1987).*

K. Tomioka et al., *J. Am. Chem. Soc.,* 109:6213–6215 (1987).

G. Cainelli et al., *Synthesis,* pp. 45–58 (1989).

P. Salvadori et al., *Tetrahedron,* 43(21):4869–4978 (1987).

M. Inagaki et al.,*Bull. Chem. Soc. Jpn.,* 60:4121–4126 (1987).

N. Kobayashi and K. Iwai, *J. Am. Chem. Soc.,* 100(22):7071–7072 (1978).

P. Hodge et al., *J. Chem. Soc. Perkin Trans. I,* pp. 2205–2209 (1983).

P. Hodge et al., *J. Chem. Soc. Perkin Trans. I,* pp. 2327–2231 (1985).

N. Kobayashi and K. Iwai, *Macromolecules,* 13:31—34 (1980).

K. Hermann and H. Wynberg, *Helvetica Chim. Acta,* 60:2208–2213 (1977).

N. Kobayashi and K. Iwai , *J. Polymer Sci., Polymer Chem. Ed.,* 18:223–233 (1980).

K. Yamauchi et al., *Bull. Chem. Soc. Jpn.,* 44:3186–3187 (1971).

K. Yamauchi et al., *J. Macromol. Sci–Chem.,* A10(6):9-81–991 (1976).

T. Yamashita et al., *Bull. Chem. Soc. Jpn.,* 51(4):1183–1185 (1978).

N. Kobayashi and K. Iwai, *Tetrahedron Lett.,* 21:2167–2170 (1980).

N. Kobayashi and K. Iwai, *J. Polymer Sci., Polym. Lett. Ed.,* 18(6):417–420 (1980).

N. Kobayashi and K. Iwai, *J. Polylm. Sci., Polym. Letter. Ed.,* 20(2):85–90 (1982).

N. Kobayashi and K. Iwai , *Polymer Journal,* 13(3):263–271 (1981).

N. Kobayashi and K. Iwai, *J. Polym. Sci., Polym. Chem. Ed.,* 18(3) 923–932 (1980).

METHODS FOR CATALYTIC ASYMMETRIC DIHYDROXYLATION OF OLEFINS

FUNDING

Work described herein was supported by a grant from the National Institutes of Health and the National Science Foundation.

RELATED APPLICATIONS

This is a continuation-in-part of application U.S. Ser. No. 07/250,378 filed Sep. 28, 1988, U.S. Pat. No. 4,965,364, which is a continuation-in-part of U.S. Ser. No. 159,068, filed Feb. 23, 1988, U.S. Pat. No. 4,871,855, which is a continuation-in-part of application U.S. Ser. No. 142,692, filed Jan. 11, 1988 abandoned, all of the above are hereby incorporated by reference herein.

BACKGROUND

In nature, the organic constituents of animals, microorganisms and plants are made up of chiral molecules, or molecules which exhibit handedness. Enantiomers are stereoisomers or chiral molecules whose configurations (arrangements of constituent atoms) are mirror images of each other; absolute configurations at chiral centers are determined by a set of rules by which a priority is assigned to each substituent and are designated R and S. The physical properties of enantiomers are identical, except for the direction in which they rotate the plane of polarized light: one enantiomer rotates plane-polarized light to the right and the other enantiomer rotates it to the left. However, the magnitude of the rotation caused by each is the same.

The chemical properties of enantiomers are also identical, with the exception of their interactions with optically active reagents. Optically active reagents interact with enantiomers at different rates, resulting in reaction rates which may vary greatly and, in some cases, at such different rates that reaction with one enantiomer or isomer does not occur. This is particularly evident in biological systems, in which stereochemical specificity is the rule because enzymes (biological catalysts) and most of the substrates on which they act are optically active.

A mixture which includes equal quantities of both enantiomers is a racemate (or racemic modification). A racemate is optically inactive, as a result of the fact that the rotation of polarized light caused by a molecule of one isomer is equal to and in the opposite direction from the rotation caused by a molecule of its enantiomer. Racemates, not optically active compounds, are the products of most synthetic procedures. Because of the identity of most physical characteristics of enantiomers, they cannot be separated by such commonly used methods as fractional distillation (because they have identical boiling points), fractional crystallization (because they are equally soluble in a solvent, unless it is optically active) and chromatography (because they are held equally tightly on a given adsorbent, unless it is optically active). As a result, resolution of a racemic mixture into enantiomers is not easily accomplished and can be costly and time consuming.

Recently, there has been growing interest in the synthesis of chiral compounds because of the growing demand for complex organic molecules of high optical purity, such as insect hormones and pheromones, prostaglandins, antitumor compounds, and other drugs. This is a particularly critical consideration, for example, for drugs because in living systems, it often happens that one enantiomer functions effectively and the other enantiomer has no biological activity and/or interferes with the biological function of the first enantiomer.

In nature, the enzyme catalyst involved in a given chemical reaction ensures that the reaction proceeds asymmetrically, producing only the correct enantiomer (i.e., the enantiomer which is biologically or physiollogically functional). This is not the case in laboratory synthesis, however, and, despite the interest in and energy expended in developing methods by which asymmetric production of a desired chiral molecule (e.g., of a selected enantiomer) can be carried out, there has been only limited success.

In addition to resolving the desired molecule from a racemate of the two enantiomers, it is possible for example, to produce selected asymmetric molecules by the chiral pool or template method in which the selected asymmetric molecule is "built" from pre-existing. naturally-occurring asymmetric molecules. Asymmetric homogeneous hydrogenation and asymmetric epoxidation have also been used to produce chiral molecules. Asymmetric hydrogenation is seen as the first manmade reaction to mimic naturally-occurring asymmetric reactions. Sharpless, K. B., *Chemistry in Britain,* January 1986, pp 38–44; Mosher H. S. and J. D. Morrison, *Science,* 221:1013–1019 (1983); Maugh, T. H., *Science, b 221:351-354* (1983); Stinson, S., *Chemistry and Engineering News,* :24 (Jun. 2, 1986).

Presently-available methods of asymmetric synthesis are limited in their applicability, however. Efficient catalytic asymmetric synthesis reactions are very rare; they require a directing group and thus are substrate limited. Because such reactions are rare and chirality can be exceptionally important in drugs, pheromones and other biologically functional compositions, a catalytic method of asymmetric dihydroxylation would be very valuable. In addition, many naturally-occurring products are dihydroxylated or can be easily derived from a corresponding vicinal diol derivative.

SUMMARY OF THE INVENTION

Olefins or alkenes with or without proximal heteroatom-containing functional groups, are asymmetrically dihydroxylated oxyaminated or diaminated using an osmium-catalyzed process which is the subject of the present invention. Chiral ligands which are novel alkaloid derivatives, particularly dihydroquinidine derivatives or dihydroquinine derivatives, useful in the method of the present invention are also the subject of the present invention. The parent alkaloids, e.g. quinidine or quinine, can also be used, but the rate of catalysis is slightly slower.

In one embodiment of the present invention, the chiral ligand is immobilized to or incorporated within a polymer. Both monomeric and polymeric ligands can be immobilized to or incorporated into the polymer. The immobilized or incorporated ligands form a complex with the osmium catalyst during the reaction, resulting in efficient catalysis in which the complex can be preserved after the reaction, allowing repetitive use of the complex. Alternatively, a preformed osmium-ligand complex can be used in the reaction, and recovered.

In the method of asymmetric modification or addition of the present invention, an olefin, a selected chiral ligand, an organic solvent, water, an oxidant, an osmium source and, optionally, an additive which accelerates hydrolysis of the osmate intermediate are combined, under conditions appropriate for reaction to occur. The method of ligand-accelerated catalysis of the present invention is useful to effect asymmetric dihydroxylation, asymmetric oxyamination and asymmetric diamination of an olefin of interest. A particular advantage of the catalytic asymmetric method is that only small quantities of osmium catalyst ar required.

DETAILED DESCRIPTION OF THE INVENTION

Asymmetric epoxidation has been the subject of much research in the past eight years. Earlier work demonstrated that the titanium-tartrate epoxidation catalyst is actually a complex mixture of epoxidation catalysts in dynamic equilibrium with each other and that the main species present (i.e., the 2:2 structure) is the best catalyst (i.e., about six times more active than titanium isopropoxide bearing no tartrate). This work also showed that this rate advantage is essential to the method's success because it ensures that the catalysis is channeled through a chiral ligand-bearing species.

The reaction of osmium tetroxide ($OsO_4$) with olefins is a highly selective and reliable organic transformation. It has long been known that this reaction is accelerated by nucleophilic ligands. Criegee, R. *Justus Liebigs Ann. Chem.*, 522:75 (1936); Criegee. R. et al., *Justus Liebigs Ann. Chem.*, 550:99 (1942); VanRheenen et al., *Tetrahedron Lett.*, 1973 (1976). It has now been shown that a highly effective osmium-catalyzed process can be used to replace previously known methods, such as the stoichiometric asymmetric osmylation method. Hentges, S. G. and K. B. Sharpless, *Journal of the American Chemical Society*, 102:4263 (1980). The method of the present invention results in asymmetric induction and enhancement of reaction rate by binding of a selected ligand. Through the use of the ligand-accelerated catalytic method of the present invention, asymmetric dihydroxylation, asymmetric diamination or asymmetric oxyamination can be effected.

As a result of this method two hydroxyl groups are stereospecifically introduced into (imbedded in) a hydrocarbon framework, resulting in cis vicinal dihydroxylation. The new catalytic method of the present invention achieves substantially improved rates and turnover numbers (when compared with previously-available methods), as well as useful levels of asymmetric induction. In addition, because of the improved reaction rates and turnover numbers, less osmium catalyst is needed in the method of the present invention than in previously-known methods. As a result, the expense and the possible toxicity problem associated with previously-known methods are reduced. Furthermore the invention allows the recovery and reuse of osmium, which reduces the cost of the process.

The method of the present invention is exemplified below with particular reference to its use in the asymmetric dihydroxylation of E-stilbene ($C_6H_5CH:CHC_6H_5$) and trans-3-hexene ($CH_3CH_2CH:CHCH_2CH_3$). The method can be generally described as presented below and that description and subsequent exemplification not only demonstrate the dramatic and unexpected results of ligand-accelerated catalysis, but also make evident the simplicity and effectiveness of the method.

Figure 1:
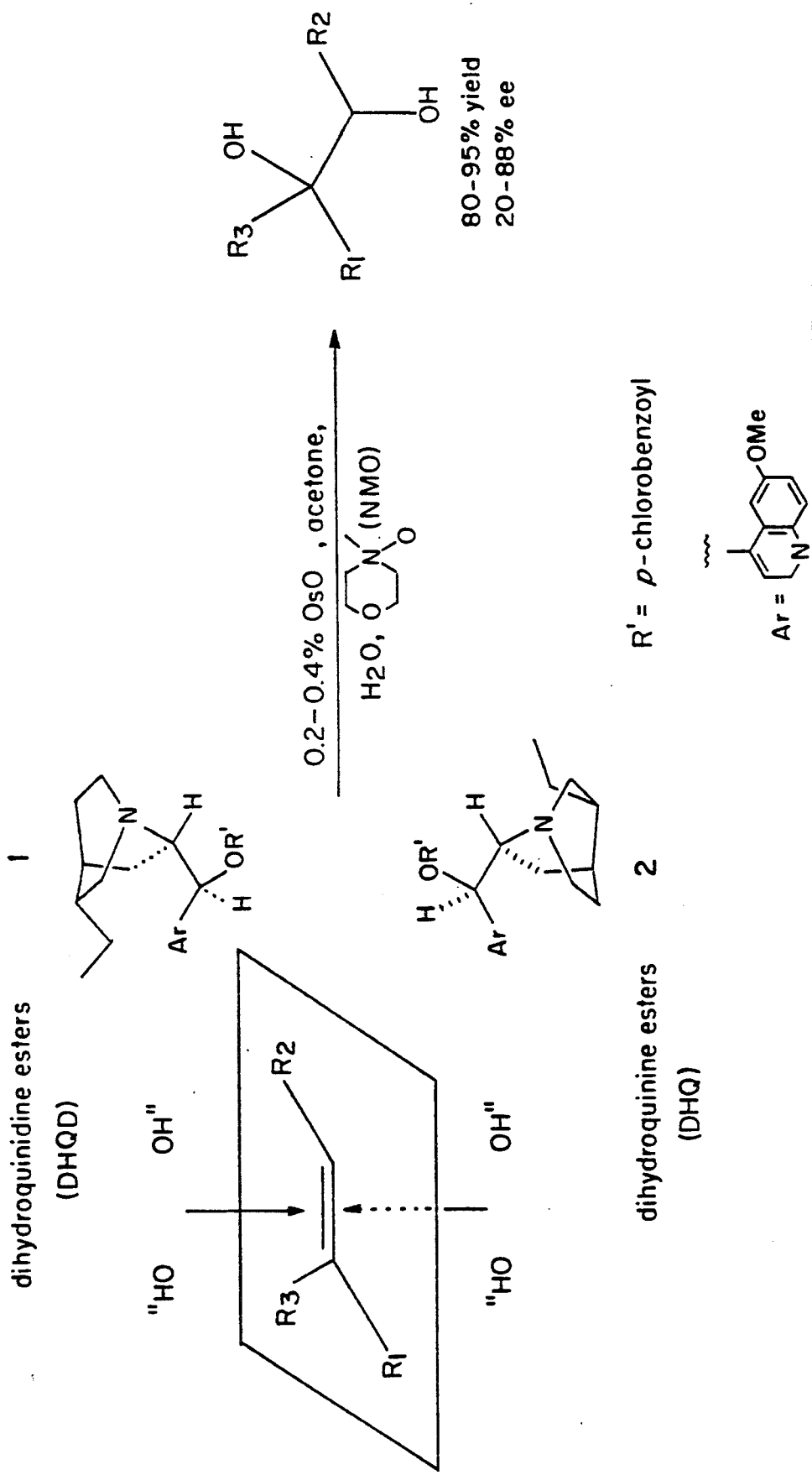
FIG. 1 is a schematic representation of asymmetric dihydroxylation via ligand-accelerated catalysis which is carried out by the method of the present invention.

The asymmetric dihydroxylation method of the present invention is represented by the scheme illustrated in FIG. 1. According to the method of the present invention, asymmetric dihydroxylation of a selected olefin is effected as a result of ligand-accelerated catalysis. That is, according to the method, a selected olefin is combined, under appropriate conditions, with a selected chiral ligand (which in general will be a chiral substituted quinuclidine), an organic solvent, water, an oxidant and osmium tetroxide and, optionally, a compound which promotes hydrolysis of the products from the osmium. Acids or bases can be used for this purpose. In one embodiment, a selected olefin, a chiral ligand, an organic solvent, water and an oxidant are combined, after the olefin and other components are combined, $OsO_4$ is added. The resulting combination is maintained under conditions (e.g., temperature, agitation, etc.) conducive for dihydroxylation of the olefin to occur. Alternatively, the olefin, organic solvent, chiral ligand, water and $OsO_4$ are combined and the oxidant added to the resulting combination. These additions can occur very close in time (i.e., sequentially or simultaneously).

In a preferred embodiment of the present invention, components of the reaction mixture are combined, to form an initial reaction combination, and olefin is added slowly to it, generally with frequent or constant agitation, such as stirring. In this embodiment, designated the "slow addition" method, organic solvent, chiral ligand, water, $OsO_4$ and the oxidant are combined. The olefin can then be slowly added to the other reactants. It is important that agitation, preferably stirring, be applied during the olefin addition. Surprisingly, for many, if not most olefins, slow addition of the olefin to the initial combination results in much better enantiomeric excess (ee), and a faster rate of reaction than the above-described method (i.e., that in which all the olefin is present at the beginning of the reaction). The beneficial effects (i.e., higher ee's) of slow olefin addition are shown in Table 3 (Column 6). A particular advantage of this slow-addition method is that the scope of the types of olefins to which the asymmetric dihydroxylation method can be applied is greatly broadened. That is, it can be applied to simple hydrocarbon olefins bearing no aromatic substituents, or other functional groups. In this process, the olefin is added slowly (e.g., over time), as necessary to maximize ee. This method is particularly valuable because it results in higher ee's and faster reaction times.

In another preferred embodiment of the present method, the chiral ligands are immobilized or incorporated into a polymer, thereby immobilizing the ligands. Both monomers and polymers of alkaloid ligands can be immobilized. The immobilized ligands form a complex with the osmium catalyst, which results in formation of an osmium catalyst complex which can be recovered after the reaction. The OsO4 polymer complex is reversible and can be used for iterative processes without washing or other treatment. The complex can be recovered, for example, by filtration or centrifugation. By employing alkaloid derivatives, heterogeneous catalytic asymmetric dihydroxylation is achieved with good to excellent enantioselectivities in the dihydroxylation of olefins.

Alternatively, alkaloid polymers can be used as ligands. Alkaloid polymers which can be used are described, for example, by Kobayashi and Iwai in *Tetrahedron Letters*, 21:2167–2170 (1980) and *Polymer Journal*, 13(3):263–271 (1981); by vonHermann and Wynberg in *Helvetica Chimica Acta*, 60:2208–2212 (1977); and by Hodge et al., *J. Chem. Soc. Perkin Trans. I*, (1983) pp. 2205–2209. Both alkaloid polymer ligands and immobilized ligands form a complex with the osmium in situ. The term "polymeric", as used herein is meant to include monomers or polymers of alkaloid ligands which are chemically bonded or attached to a polymer carrier, such that the ligand remains attached under the conditions of the reaction, or ligands which are copolymerized with one or more monomers (e.g., acrylonitrile) to form a co-polymer in which the alkaloid is incorporated into the polymer, or alkaloid polymers as described above, which are not immobilized or copolymerized with another polymer or other carrier.

Industrial scale syntheses of optically active vicinal diols are possible using polymeric ligands. The convenience and economy of the process is enhanced by recycling the alkaloid-OsO4 complex. This embodiment of the present method allows efficient heterogeneous asymmetric dihydroxylation utilizing polymeric or immobilized cinchona alkaloid derivatives.

Polymeric cinchona alkaloids which are useful in the present method can be prepared by art-recognized techniques. See, for example, Grubhofer and Schleith, *Naturwissenschaften*, 40:508 (1953); Yamauchi et al., *Bull. Chem. Soc. Jpn.*, 44:3186 (1971); Yamauch et al., *J. Macromal. Sci. Chem.*, A10:981 (1976). A number of different types of polymers that incorporate dihydroquinidine or dihydroquinine derivatives can be used in this process. These polymers include: (a) co-polymers of cinchona alkaloid derivatives with co-polymerizing reagents, such as vinyl chloride, styrene acrylamide, acrylonitrile, or acrylic or methacrylic acid esters; (b) cross-linked polymers of cinchona alkaloid derivatives with cross linking reagents, such as 1,4-divinylbenzene, ethylene glycol bismethacrylate; and (c) cinchona alkaloid derivatives covalently linked to polysiloxanes. The connecting point of the polymer backbone to the alkaloid derivative can be at C(10), C(11), C(9)-O,N(1'), or C(6')-O as shown below for both quinidine and quinine derivatives. Table 3 shows the examples of the monomeric alkaloid derivatives which can be incorporated in the polymer system.

For example, a polymer binding dihydroquinidine was prepared by copolymerizing 9-(10-undecenoyl)-dihydroquinidine in the presence of acrylonitrile (5 eq); a 13% yield was obtained exhibiting 4% alkaloid incorporation This polymer, an acrylonitrile co-polymer of 9-(10-undecenoyl)-10,11-dihydroquinidine, is shown as polymer 4 in Table 1, below. Three other polymers, an acrylonitrile co-polymer of 9-(4-chlorobenzoyloxy)quinine, (polymer 1, Table 3) an acrylonitrile co-polymer of 11-[2-acryloyloxy)ethylsulfinyl]-9-(4-chlorobenzoyloxy)-10,11-dihydroquinine (polymer 2, Table 1) and an acrylonitrile co-polymer of 11-[2-acryloyloxy)-ethylsulfonyl]-9-(N,N-dimethylcarbamoyl)-10,11-dihydroquinidine, (polymer 3, Table 1) were prepared according to the procedures of Inaguki et al., or slightly modified versions of this procedure. See, Inaguki et al., *Bull. Chem. Soc. Jpn.*, 60:4121 (1987). Using these polymers, the asymmetric dihydroxylation of trans-stilbene was carried out. The results are summarized in Table 1. Good to excellent asymmetric induction and reasonable reaction rates were observed. As shown in Table 1, reaction with polymer 2 exhibited the highest degree of asymmetric induction. The activity of the OsO4-polymer complex is preserved after the reaction, thus allowing repetitive use of the complex. This reaction can be carried out with terminal and aliphatically substituted olefins to show good yields and enantioselectivities (for example, styrene with polymer 2, 60% ee, 68% yield, and ethyltrans-2-octenoate with polymer 3. 60% ee, 85% yield) and the same process can be applied to a variety of different olefins.

TABLE 1

Heterogeneous Catalytic Asymmetric Dihydroxylation of trans-Stilbene Using Various Polymeric Alkaloids

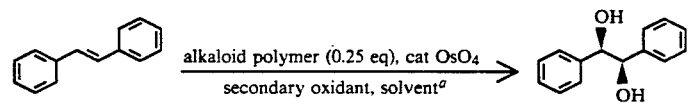

| Entry | Polymers | OsO4 | Secondary Oxidant | Reaction Temp | Reaction Time | Yield (%) | ee (%) |
| --- | --- | --- | --- | --- | --- | --- | --- |
| 1 | 1 | 1 mol % | NMO | rt | 7d | 68 | — |
| 2 | 2 | 1 mol % | NMO | 10° C. | 2-3d | 81-87 | 85-93[b] |
| 3 | 2 | 1 mol % | NMO | rt | 24 h | 81 | 82 |
| 4 | 2 | —[c] | NMO | rt | 36 h | 75 | 78 |
| 5 | 3 | 1 mol % | NMO | 0° C. | 48 h | 85 | 80 |
| 6 | 3 | 1.25 mol % | K3Fe(CN)6 | rt | 18 h | 96 | 87 |
| 7 | 4 | 1 mol % | NMO | 10° C. | 48 h | 87 | 82 |

TABLE 1-continued
Heterogeneous Catalytic Asymmetric
Dihydroxylation of trans-Stilbene Using Various Polymeric Alkaloids

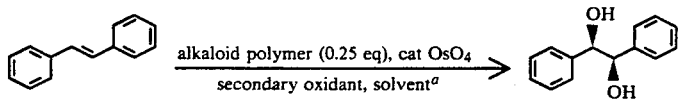

| Entry | Polymers | O$_s$O$_4$ | Secondary Oxidant | Reaction Temp | Reaction Time | Yield (%) | ee (%) |
|---|---|---|---|---|---|---|---|
| 8 | 4 | 1.25 mol % | K$_3$Fe(CN)$_6$ | rt | 48 h | 91 | 86 |

[a]General procedure is set out in detail in Example 14. With N-methylmorpholine-N-oxide (NMO) acetone/water (10/1, v/v) was the solvent and ferricyanide tert-butyl alcohol/water (1/1, v/v) was used as solvent.
[b]Results vary slightly depending on different batches of polymer 2.
[c]Reaction was carried out with polymer 2 which had been used in entry 3 without further addition of O$_s$O$_4$.

In another embodiment of the present method, an additive which accelerates hydrolysis of the osmate ester intermediates can, optionally, be added to the reaction combination. These additives can be acids or bases, for example. Bases are preferred for this purpose. For example, soluble, carboxylic acid salts with organicsolubilizing counter-ions, (e.g., tetraalkyl ammonium ions) are useful. Carboxylate salts which are preferred in the present reaction are soluble in organic media and in organic/aqueous co-solvent systems. For example, tetraethyl ammonium acetate has been shown to enhance the reaction rate and ee of some olefins (Table 5). The additive does not replace the alkaloid in the reaction. Compounds which can be used include benzyltrimethyl, ammoniumacetate, tetramethylammonium acetate and tetraethylammonium acetate. However, other oxyanion compounds (e.g., sulfonates, carbonates, borates or phosphates) may also be useful in hydrolyzing the osmate ester intermediates. The compound can be added to the reaction combination of organic solvent, chiral ligand, water and OsO$_4$ in a reaction vessel, before olefin addition. It is important to agitate (e.g., by stirring) the reaction combination during olefin addition. The additive can also be added to the reaction combination, described above, wherein all of the olefin is added at the beginning of the reaction. In one embodiment, the amount of additive is generally approximately 2 equivalents; in general from about 1 to about 4 equivalents will be used.

In another embodiment of the present invention, the process can be run in an organic non-polar solvent such as toluene. This embodiment is particularly useful in the slow addition method. Preferably, a carboxylate compound which accelerates hydrolysis of the osmate ester intermediates (e.g., tetraethyl or tetramethyl ammonium acetate) is added. This embodiment is designated the "phase transfer" method. In this embodiment olefins which are not soluble, or have limited solubility, in mixtures of acetone/water or acetonitrile/water, are dissolved in toluene and then added slowly a mixture of organic solvent, chiral ligand, water and OsO$_4$. The carboxylate salt serves the dual function of solubilizing the acetate ion in the organic phase where it can promote hydrolysis of the osmate ester, and carrying water associated with it into the organic phase, which is essential for hydrolysis. Higher ee's are obtained with many substrates using this method.

In a further embodiment of the present invention, a boric acid or a boric acid derivative (R—B(OH)$_2$, R=alkyl, aryl or OH), such as boric acid itself (i.e., B(OH)$_3$) or phenylboric acid (i e., Ph—B(OH)$_2$), can be added to the reaction mixture. In the slow addition method, the boric acid is added to the ligand-organic solvent-OsO$_4$ mixture prior to the addition of the olefin. The amount of boric acid added is an amount sufficient to form the borate ester of the diol produced in the reaction. Without wishing to be bound by theory, it is believed that the boric acid hydrolyzes the osmium ester and captures the diols which are generated in the reaction. Neither water nor a soluble carboxylate such as tetraalkyl ammonium carboxylate, is required to hydrolyze the osmium ester in the present reactions. Because the presence of water can make the isolation and recovery of water-soluble diols difficult, the addition of a boric acid makes isolation of these diols easier. Especially, in the case of an aryl or alkyl boric acid, it is easy because, in place of the diol, the product is the cyclic borate ester which can be subsequently hydrolyzed to the diol. Iwasawa et al., *Chemistry Letters*, pp. 1721–1724 (1988). The addition of a boric acid is particularly useful in the slow addition method.

In another embodiment of the present method, oxidants such as potassium hexacyanoferrate (III) (potassium ferricyanide, K$_3$Fe(CN)$_6$) is added to the reaction as a reoxidant. In a preferred embodiment, at least two equivalents of the oxidant (based on the amount of olefin substrate) is added to the reaction. It is crucial that an equivalent amount of a base, such as potassium carbonate (KCO$_3$), is added in conjunction with the reoxidant. High enantioselectivities are obtained in catalytic asymmetric dihydroxylations using K$_3$Fe(CN)$_6$ as the reoxidant.

The use of potassium ferricyanide in a stoichiometric amount as an oxidant for non-asymmetric osmiumcatalyzed dihydroxylation of olefins was reported by Minato, Yamamoto and Tsuji in *J. Org. Chem.*, 55:766 (1990). The addition of K$_3$Fe(CN)$_6$ (in conjunction with the base) results in an improvement in the ability of the present catalytic system to turn over, even in the presence of quinuclidine, a ligand which strongly inhibits catalysis when other oxidants are used, e.g. N-methylmorpholine-N-oxide (NMO). In the present embodiment, potassium ferricyanide and potassium carbonate were added to the present cinchona alkaloid based asymmetric dihydroxylation process and the outcome was unexpected (i.e. not just another way to reoxidize the osmium and/or achieve better turnover with difficult substrates). As shown in Table 2, the use of potassium ferricyanide/potassium carbonate in place of NMO leads to across-the-board increases in the level of asymmetric induction for most olefins. The first two columns of data shown in Table 2 are for results employing NMO with and without "slow addition" of olefin, respectively. The third column reveals the results obtained using $K_3Fe(CN)_6$ with the same substrates and without "slow addition" of the olefin. The improvements of enantioselectivity are great as evidenced by the fact that the previous results (shown in Table 2) were obtained at 0° C. while the ferricyanide experiments were performed at room temperature. The ferricyanide reactions can be run at a range of temperatures, however, depending upon the substrate.

late a chiral olefin, one enantiomer will be more reactive than the other. As a result, it is possible to separate or kinetically resolve the enantiomorphs. That is, through use of appropriately-selected reactants, it is possible to separate the asymmetrically dihydroxylated product from the unreacted starting material and both the product and the recovered starting material will be enantiomerically enriched.

TABLE 2

Percentage enantiomeric excesses of diols obtained in the asymmetric dihydroxylation of olefins under different catalytic conditions using dihydroquinidine p-chlorobenzoate as the chiral ligand.

$$R\diagup\!\!\!\diagdown R' \longrightarrow R\underset{OH}{\overset{OH}{\diagup\!\!\!\diagdown}} R'$$

| entry | olefins | NMO[a] ee (%) (slow addition) | NMO[a] ee (%) (no slow addition) | $K_3Fe(CN)_6$[b] ee (%) (no slow addition) |
|---|---|---|---|---|
| 1 | styrene (PhCH=CH$_2$) | 60 | 56 | 73 |
| 2 | trans-stilbene (PhCH=CHPh) | 95 | 78 | 99 |
| 3 | β-methylstyrene (PhCH=CHCH$_3$) | 86 | 65 | 91 |
| 4 | PhCH=CHCH$_2$OAc | 79 | 76 | 91 |
| 5 | PhCH=CHCO$_2$Me | 86 | 60 | 95 |
| 6 | trans-alkene (long chain) | 69 | 20 | 74 |

[a]Reactions were carried out in acetone-water, 10:1 v/v, at 0° C.
[b]Reactions were carried out in tert-butyl alcohol-water 1:1 v/v, at ambient temperature. In all cases the isolated yield was 85%–95%.

The amount of water added to the reaction mixture is an important factor in the present method. The optimum amount of water to be added can be determined empirically and, in general, should be that amount which results in maximum ee. Generally, approximately 10 to 16 equivalents of water can be added, preferably 13 to 14 equivalents should be used.

An olefin of interest can undergo asymmetric dihydroxylation according to the present invention. For example, any hydrocarbon containing at least one carbon-carbon double bond as a functional group can be asymmetrically dihydroxylated according to the subject method. The method is applicable to any olefin of interest and is particularly well suited to effecting asymmetric dihydroxylation of prochiral olefins (i.e., olefins which can be converted to products exhibiting chirality or handedness). In the case in which the method of the present invention is used to asymmetrically dihydroxy- The chiral ligand used in the asymmetric dihydroxylation method will generally be an alkaloid, or a basic nitrogenous organic compound, which is generally heterocyclic. The chiral ligand can be a naturally occurring or purely synthetic compound. The optimum derivative which is used can be determined based upon the process conditions for each reaction. Examples of alkaloids which can be used as the chiral ligand in the asymmetric dihydroxylation method include cinchona alkaloids, such as quinine, quinidine, cinchonine, and cinchonidine. Examples of alkaloid derivatives useful in the method of the present invention are shown in Table 3. As described in detail below, the two cinchona alkaloids quinine and quinidine act more like enantiomers than like diastereomers in the scheme represented in FIG. 1.

As represented in FIG. 1, and as shown by the results in Table 4, dihydroquinidine derivatives (represented as DHQD) and dihydroquinine derivatives (represented as DHQ) have a pseudo-enantiomeric relationship in the present method (DHQD and DHQ are actually diastereomers). That is, they exhibit opposite enantiofacial selection. Such derivatives can be, for example, esters or ethers, although other forms can be used. The choice of derivative depends upon the process. When dihydroquinidine is used as the ligand, delivery of the two hydroxyl groups takes place from the top or upper face (as represented in FIG. 1) of the olefin which is being dihydroxylated. That is, in this case direct attack of the re- or re-re- face occurs. In contrast, when the dihydroquinine derivative is the ligand used, the two hydroxyl groups are delivered from the bottom or lower (si- or si-si-face) face of the olefin, again as represented in FIG. 1. This is best illustrated by reference to entries 1, 2 and 5 of Table 4. As shown, when DHQD (dihydroquinidine esters) is used, the resulting diol has an R or R,R configuration and when ligand 2 (dihydroquinine esters) is used, the resulting diol has an S or S,S configuration.

TABLE 3

Alkaloid Derivatives

| R | Dihydroquinidine Derivative | Yield (%) | % ee |
|---|---|---|---|
| 3-ClC$_6$H$_4$ | 3-chlorobenzoyl | 89 | 96.5 |
| 2-MeOC$_6$H$_4$ | 2-methoxybenzoyl | 89 | 96 |
| 3-MeOC$_6$H$_4$ | 3-methoxybenzoyl | 87 | 96.7 |
| 2-C$_{10}$H$_7$ | 2-napthoyl | 95.4 | 98.6 |
| C$_6$H$_{11}$ | cyclohexanoyl | 90 | 91 |
| 4-PhC$_6$H$_4$ | 4-phenylbenzoyl | 89 | 96 |
| 2,6-(MeO)$_2$C$_6$H$_3$ | 2,6-dimethoxybenzoyl | 88 | 92 |
| 4-MeOC$_6$H$_4$ | 4-methoxyenzoyl | 91 | 97.6 |
| 4-ClC$_6$H$_4$ | 4-chlorobenzoyl | 93 | 99 |
| 2-ClC$_6$H$_4$ | 2-chlorobenzoyl | 87 | 94.4 |
| 4-NO$_2$C$_6$H$_4$ | 4-nitrobenzoyl | 71 | 93 |
| C$_6$H$_5$ | benzoyl | 92 | 98 |
| Me$_2$N | dimethylcarbamoyl | 96 | 95 |
| Me | acetyl | 72 | 94 |
| MeOCH$_2$ | α-methoxyacetyl | 66 | 93 |
| AcOCH$_2$ | α-acetoxyacetyl | 96 | 82.5 |
| Me$_3$C | trimethylacetyl | 89 | 86.5 |

The example below is a phosphoryl derivative and therefore differs from the carboxylic acid ester derivatives shown above: the phosphorus atom is directly bound to the oxygen atom of the alkaloid.

| Ph$_2$P(O) | diphenylphosphinic ester | 69 | 97.5 |

TABLE 4

| Olefins | ligand; ee$^a$; confgn. of diol |
|---|---|
| (2-hexene) | DHQD; 20%, (70%, 10 h); RR<br>DHQ; (60%, 16 h); SS |
| n-Bu-CH=CH-n-Bu | DHQD; (70%, 120 h) |
| (methyl n-C$_5$H$_{11}$ alkene) | DHQD; (69%, 30 h); RR<br>DHQ; (63%, 30 h); SS |
| (2,5-dimethyl-3-hexene) | DHQD; 12%, (46%, 24 h), (76%, 24 h + 1 eq OAc) |
| (4-methyl-2-pentene) | DHQD; 37.5% |
| (2-methyl-2-hexene) | DHQD; (46%, 24 h, rt) |
| (2-methyl-2-hexene isomer) | DHQD; (40%, 24 h, rt) |
| (vinylcyclohexane) | DHQD; 46%, (50%, 20 h); R |
| (vinylcyclooctane) | DHQD; 50% |
| (3,3-dimethyl-1-butene) | DHQD; 40% |
| Cl-CH=CH-CH$_2$Cl | DHQD; 35%, (40%, 12 h) |
| styrene | DHQD; 56%, (61%, 5 h); R<br>DHQ; 54%; S |
| (o-methylstyrene) | DHQD; 53% |
| (2,3-dimethylstyrene) | DHQD; 65% |
| (2,5-dimethylstyrene) | DHQD; 63% |
| (β-methylstyrene) | DHQD; 65%, (86%, 5 h); RR<br>DHQ; 55%, (80%, 5 h); SS |

TABLE 4-continued

| Olefins | ligand; ee[a]; confgn. of diol |
|---|---|
| PhCH=CHCH₃ (cis) | DHQD; 0-10% |
| PhC(CH₃)=CH₂ | DHQD; 33%; R |
| PhCH=CHCH₃ (with methyl) | DHQD; 34%, (53%, 24 h) |
| 4-O₂N-C₆H₄-CH=CH₂ | DHQD; 51% |
| 4-MeO-C₆H₄-CH=CH₂ | DHQD; 67% |
| 3-vinylfuran | DHQD; 40% |
| trans-stilbene (Ph-CH=CH-Ph) | DHQD; 80%; 92% in the presence of 2 eq. OAc; RR<br>DHQ; 79%; SS |
| 1-phenylcyclohexene | DHQD; 10%, (78%, 26 h), (81%, 16 h + 1 eq OAc)<br>DHQ; (73%, 26 h) |
| PhCH=CHCH₂OAc | DHQD; 76%; RR |
| PhCH=CHCH₂OCOPh | DHQD; 80% |
| PhCH=CHCH₂Cl | DHQD; 60%, (78%, 10 h) |
| PhCH₂CH=CH₂ | DHQD; 20% |

| Olefins | ligand; ee[a]; confgn. of diol |
|---|---|
| PhCH₂CH=CHCH₃ | DHQD; (44%, 10 h) |
| PhO-CH₂-CH=CH₂ | DHQD; 34% |
| PhO-CH₂-C(CH₃)=CH₂ | DHQD; 27% |
| nC₁₅H₃₁-CH=CH-CO₂Me | DHQD; 38% |
| n-C₅H₁₁-CH=CH-CO₂Et | DHQD; 47.4%, (67%, 31 h) |
| CH₃CH=CH-CO₂Et | DHQD; 53% |
| CH₃CH=CH-CO₂CH₂Ph | DHQD; 45% |
| Et₃C-O-CH₂-CH(O-)-CH₂-CH=CH-CO₂Me (acetonide) | DHQD; (52% de, 31 h) |
| acetonide-CH=CH-CO₂Me | DHQD; (70% de, 42 h) |
| cyclohexyl-CH=CH-CO₂Et | DHQD; 74.3% |
| methyl cyclohex-1-enecarboxylate | DHQD; (36%, 24 h + OAc, rt) |
| PhCH=CH-CO₂Et (ethyl cinnamate) | DHQD; 92% |
| PhCH=CH-CO₂Me (methyl cinnamate) | DHQD; 91% |
| PhCH=CH-CO₂CH₂Ph | DHQD; 80-85% |

TABLE 4-continued

| Olefins | ligand; ee[a]; confgn. of diol |
|---|---|
| (E)-methyl p-methoxycinnamate | DHQD; <60%, (80%, slow addition) |
| methyl α-methylcinnamate | DHQD; (38%, toluene-water, 24 h + OAc, rt) |
| 3-methyl-2-cyclohexen-1-one | DHQD; (10%, 24 h, rt) |
| 1-acetyl-1-cyclohexene | DHQD; (36%, 24 h + OAc, rt) |
| 3-methyl-cyclohexene-1,1-dioxolane | DHQD; (37%, 12 h + OAc) |
| CH₂=CHCH(OEt)₂ | DHQD; 27%, (31%, 13 h) |
| n-C₇H₁₅-CH=CH-CH(OCH₂CH₂O) | DHQD; (56%, 20 h) (66%, 20 h + OAc) |
| n-C₅H₁₁-CH=CH-C(Me)(OCH₂CH₂O) | DHQD; (46%, 18 h) (50%, 18 h + OAc) |
| PhCH=CH-CH(OMe)₂ | DHQD; (75%, 18 h) (83%, 18 h + OAc) |
| PhCH=CH-C(Me)(OCH₂CH₂O) | DHQD; (60%, 10 h) (89%, 10 h + OAc) |
| PhCH=CH-C(Ph)(OCH₂CH₂O) | DHQD; (85%, 20 h) (87%, 20 h + OAc) |
| (Z)-4-(trimethylsilyloxy)-4-heptene | DHQD; (27%, 23 h + OAc) |
| (Z)-1-phenyl-1-(trimethylsilyloxy)-1-propene | DHQD; (72%, 23 h) (78%, 23 h + OAc) |

[a] Enantiomeric excesses in parentheses were obtained with slow addition of olefin over a period of time indicated and with stirring at 0° C. except otherwise stated. Tetraethylammonium acetate tetrahydrate were added in some cases as indicated.

TABLE 5

Enantiomeric excesses obtained in the asymmetric dihydroxylation of olefins under different conditions

| entry | olefin | stoichiometric[a] | catalytic[b] (original) | catalytic[c] (acetate) | catalytic[d] (slow addition) |
|---|---|---|---|---|---|
| 1 | styrene | 61 | 56 | 61 | 60 (5 h) |
| 2 | (E)-β-methylstyrene | 87 | 65 | 73 | 86 (5 h) |
| 3 | 1-phenylcyclohexene | 79 | 8[e] | 52 | 78 (26 h)[f] |

TABLE 5-continued

Enantiomeric excesses obtained in the asymmetric dihydroxylation of olefins under different conditions

| entry | olefin | stoichiometric[a] | catalytic[b] (original) | catalytic[c] (acetate) | catalytic[d] (slow addition) |
|---|---|---|---|---|---|
| 4 | (olefin structure) | 80 | 12[g] | 61 | 46 (24 h)[h] |
|   |   |   |   |   | 76 (24 h + OAc) |
| 5 | (olefin structure) | 69 | 20 | 64 | 70 (10 h) |

[a]All stoichiometric reactions were carried out in acetone-water, 10:1 v/v, at 0° C. and at a concentration of 0.15M in each reagent.
[b]All reactions were carried out at 0° C. according to the original procedure reported in ref. 1(a).
[c]All reactions were carried out exactly as described in ref. 1(a) (i.e. without slow addition) except that 2 eq of $Et_4NOAc·4H_2O$ were present.
[d]All reactions were carried out at 0° C. as described in note 2 for trans-3-hexene with an alkaloid concentration of 0.25M. The period for slow addition of the olefin is indicated in parentheses. The ee's shown in the Table were obtained with dihydroquinidine p-chlorobenzoate as the ligand. Under the same conditions, the pseudoenantiomer, dihydroquinine p-chlorobenzoate, provides products with ee's 5–10% lower. In all cases the isolated yield was 85–95%.
[e]This reaction took 7 days to complete.
[f]With an addition period of 16 h, ee's of 63 and 65% were obtained at 0° C. and 20° C., respectively; with the combination of slow addition over a period of 16 h and the presence of 1 eq of $Et_4NOAc·4H_2O$ at 0° C., an ee of 81% was realized.
[g]This reaction took 5 days to complete.
[h]When the reaction was carried out at 20° C. and the olefin was added over a period of 24 h, an ee of 59% was obtained.

Because of this face selection rule or phenomenon, it is possible, through use of the present method and the appropriate chiral ligand, to pre-determine the absolute configuration of the dihydroxylation product.

As is also evident in Table 4, asymmetric dihydroxylation of a wide variety of olefins has been successfully carried out by means of the present invention. Each of the embodiments described results in asymmetric dihydroxylation, and the "slow addition" method is particularly useful for this purpose. In each of the cases represented in the Table in which absolute configuration was established, the face selection "rule" (as interpreted with reference to the orientation represented in FIG. 1) applied: use of DHQD resulted in attack or dihydroxylation occurring from the top or upper face and use of DHQ resulted in attack or dihydroxylation occurring from the bottom or lower face of the olefin. This resulted, respectively, in formation of products having an R or R,R configuration and products having an S or S,S configuration.

In a preferred embodiment of the present method, aryl ethers of various cinchona alkaloids are used as ligands. A high level of asymmetric induction can be obtained using aryl ethers of dihydroquinidine or dihydroquinine as ligands. For example, aryl ethers having the following formula are particularly useful:

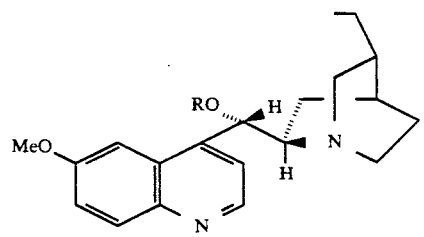

wherein R is phenyl, naphthyl, or o-methoxyphenyl. The stoichiometric asymmetric dihydroxylation of various dialkyl substituted olefins was performed using the phenyl ether derivation of dihydroquinidine. The results are shown in Table 6.

TABLE 6

Stoichiometric Asymmetric Dihydroxylation Phenyl Ether Dihydroquinidine $$R^1\text{—CH=CH—}R^2 \xrightarrow[\text{2) LiAlH}_4]{\text{1) 1 eq OsO}_4, \text{1 eq 1, in toluene}} R^1\text{—CH(OH)—CH(OH)—}R^2$$

| Entry | Olefins | Reaction temp (°C.) | % ee[a] | % ee[a] with 3 (for comparison) |
|---|---|---|---|---|
| 1 | (olefin) | 0 | 85 | 71 |
| 2 |   | −78 | 95 |   |
| 3 | (olefin) | 0 | 88 | 73 |
| 4 |   | −78 | 93 |   |
| 5 | (olefin) | 0 | 89 | 79 |
| 6 |   | −78 | 94 |   |
| 7 | (olefin)—COOEt[b] | 0 | 90 | 67 |

TABLE 6-continued

Stoichiometric Asymmetric Dihydroxylation Phenyl Ether Dihydroquinidine

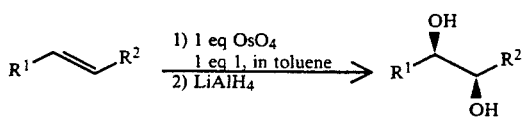

| Entry | Olefins | Reaction temp (°C.) | % ee[a] | % ee[a] with 3 (for comparison) |
|---|---|---|---|---|
| 8 | (structure with COOMe[b]) | 0 | 97[c] | 77[c] |

[a]Enantiomeric excess was determined by GLC or HPLC analysis of the bis-Mosher ester derivatives.
[b]The reaction was worked up with NaHSO₃ in H₂O-THF.
[c]Diastereomeric excess.

The reaction was performed by adding 1 eq of olefin to a 1:1 mixture of OsO₄ and the ligand dry toluene (0.1M) followed by a reductive work-up using lithium aluminum hydride (LiAlH₄) to yield the (R,R)-diol in 60-95% yield with good to excellent enantiomeric excess. Reactions with α, β-unsaturated esters also proceeded with much improved enantio- and diastereoselectivities (≧90%, as shown in entries 7 and 8, Table 6) using this ligand. By lowering the reaction temperature to −78° C., the reaction with straight chain dialkyl substituted olefins proceeded with very high enantioselectivities (≧93%, as shown in entries 2, 4 and 6 of Table 6). In the several cases which were plotted the variance in ee with temperature closely followed Arrhenius relationship.

Several dihydroquinidine aryl ether derivatives were examined as chiral ligands for the asymmetric dihydroxylation of (E)-3-hexene, as shown in Table 7, below. Reactions with all of the aryl ether derivatives tried exhibited higher enantioselectivities than the corresponding reaction with p-chlorobenzoate dihydroquinidine. The highest enantioselectivity was obtained with 9-O-(2'-methoxyphenyl)-dihydroquinidine (entry 2, Table 7).

TABLE 7

Stoichiometric Asymmetric Hydroxylation of (E)-3-hexene

| Entry | 1 | 2 | 3 | 4 | 5 |
|---|---|---|---|---|---|
| R | phenyl | 2-OMe-phenyl | 2-CF₃-phenyl | 4-MeO-phenyl | 4-O₂N-phenyl |
| % ee | 85 | 88 | 81 | 76 | 75 |

In one embodiment of the present method, aryl ether ligands were used in the catalytic asymmetric dihydroxylation of (E)-3-hexene. In this embodiment, the results are summarized in Table 8. The catalytic asymmetric dihydroxylation reactions (entries 1–3, Table 8) were carried out by slow addition of (E)-3-hexene (1 eq) to a mixture of phenyl ether dihydroquinidine (0.25 eq), N-methyloorpholine N-oxide (NMO, 1.5 eq) and OsO₄ (0.004 eq) in acetone-water (10/1, v/v) at 0° C., followed by work-up with Na₂S₂O₅. The reaction proceeded faster upon addition of tetraethylammonium acetate (2 eq) to the reaction mixture (entry 4, Table 8). Potassium ferricyanide was added as the secondary oxidant (entries 5 and 6, Table 8). In these cases, slow addition of olefin was not required. To a mixture of (E)-3-hexane (1 eq), aryl ether of dihydroquinidine (0.25 eq), K₃Fe(CN)₆ (3 eq) and potassium carbonate (K₂CO₃ 3 eq) in tert-butyl alcohol-water (1/1, v/v) was added OsO₄ (0.0125 eq); the resulting mixture was stirred at room temperature for 20 hours. Reductive work-up (with $Na_2SO_3$) gave the diol in 85–90% yield with essentially the same ee as that obtained in the stoichiometric reaction.

TABLE 8

Catalytic Asymmetric Dihydroxylation of (E)-3-hexene

| Entry | Ligand | $OsO_4$ | Secondary oxidant | Additive | Reaction Temp (°C.) | Reaction Time (hr) | % ee |
|---|---|---|---|---|---|---|---|
| 1 | 1 | 0.4 mol % | NMO | | | 16 | 70 |
| 2 | 1 | 0.4 | NMO | | 0 | 30 | 75 |
| 3 | 1 | 0.4 | NMO | | 0 | 120 | 85 |
| 4 | 1 | 0.4 | NMO | $Et_4NOAc$ | 0 | 16 | 82 |
| 5 | 1 | 1.25 | $K_3Fe(CN)_6$ | $K_2CO_3$ | rt | 20 | 83 |
| 6 | 2 | 1.25 | $K_3Fe(CN)_6$ | $K_2CO_3$ | rt | 20 | 89 |

Enantioselectivities in the dihydroxylation of dialkyl substituted olefins, which were previously only possible through the use of stoichiometric reagents at low temperature, can now be obtained in the catalytic asymmetric dihydroxylation using these aryl ether ligands at room temperature.

In general, the concentration of the chiral ligand used will range from 0.01M to 2.0M. In one embodiment, exemplified below, the solution is 0.261M in alkaloid 1 (the dihydroquinidine derivative). In one embodiment of the method, carried out at room temperature, the concentrations of each alkaloid represented in FIG. 1 is at 0.25M. In this way, the enantiomeric excess resulting under the conditions used is maximized. The amount of chiral ligand necessary for the method of the present invention can be varied as the temperature at which the reaction occurs varies. For example, it is possible to reduce the amount of alkaloid (or other chiral ligand) used as the temperature at which the reaction is carried out is changed. For example, if it is carried out, using the dihydroquinidine derivative, at 0° C., the alkaloid concentration can be 0.15M. In another embodiment, carried out at 0° C., the alkaloid concentration was 0.0625M.

Many oxidants (i.e., essentially any source of oxygen) can be used in the present method. For example, amine oxides (e.g., trimethyl amine oxides), tert-butyl hydroperoxide, hydrogen peroxide and oxygen plus metal catalysts (e.g., copper ($Cu^+$-/$Cu^{++}$/$O_2$), platinum ($Pt/O_2$), palladium ($Pd/O_2$) can be used. In one embodiment of the invention N-methylmorpholine N-oxide (NMO) is used as the oxidant. NMO is available commercially (e.g., Aldrich Chemicals, 97% NMO anhydrous, or as a 60% solution in water). In addition, as stated above, potassium ferricyanide can be used in lieu of the amine oxide. Potassium ferricyanide is an efficient oxidant in the present method.

Osmium will generally be provided in the method of the present invention in the form of osmium tetroxide ($OsO_4$), although other sources (e.g. osmium trichloride anhydrous, osmium trichloride hydrate) can be used. $OsO_4$ can be added as a solid or in solution.

The osmium catalyst used in the method of the present invention can be recycled, for re-use in subsequent reactions. This makes it possible not only to reduce the expense of the procedure, but also to recover the toxic osmium catalyst. For example, the osmium catalyst can be recycled as follows: Using reduction catalysts (e.g., Pd-C), the osmium VIII species is reduced and adsorbed onto the reduction catalyst. The resulting solid is filtered and resuspended. NMO (or an oxidant), the alkaloid and the substrate (olefin) are added, with the result that the osmium which is bound to the Pd/C solid is reoxidized to $OsO_4$ and re-enters solution and plays its usual catalytic role in formation of the desired diol. This procedure (represented below) can be carried out through several cycles, thus re-using the osmium species The palladium or carbon can be immobilized, for example, in a fixed bed or in a cartridge.

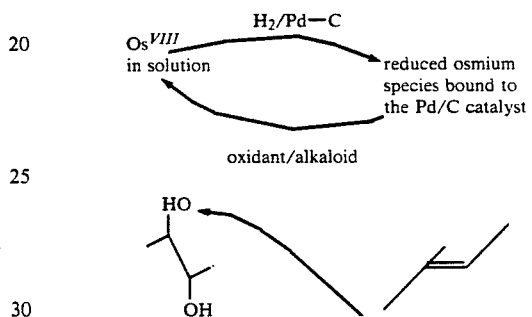

In one embodiment an olefin, such as recrystallized trans-stilbene ($C_6H_5CH:CHC_6H_5$), is combined with a chiral ligand (e.g., p-chlorobenzoyl hydroquinidine), acetone, water and NMO. The components can be added sequentially or simultaneously and the order in which they are combined can vary. In this embodiment, after the components are combined, the resulting combination is cooled (e.g., to approximately 0° C. in the case of trans-stilbene); cooling can be carried out using an ice-water bath. $OsO_4$ is then added (e.g., by injection), in the form of a solution of $OsO_4$ in an organic solvent (e.g., in toluene). After addition of $OsO_4$, the resulting combination is maintained under conditions appropriate for the dihydroxylation reaction to proceed.

In another preferred embodiment, a chiral ligand (e.g., dihydroquinidine 4-chlorobenzoate), NMO, acetone, water and $OsO_4$ (as a 5M toluene solution) are combined. The components can be added sequentially or simultaneously and the order in which they are combined can vary. In this embodiment, after the components are combined, the resulting combination is cooled (e.g., to approximately 0° C.); cooling can be carried out using an ice-water bath. It is particularly preferred that the combination is agitated (e.g., stirred). To this well-stirred mixture, an olefin (e.g., trans-3-hexene) is added slowly (e.g., by injection). The optimum rate of addition (i.e., giving maximum ee), will vary depending on the nature of the olefinic substrate. In the case of trans-3-hexene the olefin was added over a period of about 16–20 hours. After olefin addition, the mixture can be stirred for an additional period of time at the low temperature (1 hour in the case of trans-3-hexene). The slow-addition method is preferred as it results in better ee and faster reaction times.

In another embodiment, a compound which accelerates hydrolysis of the osmate ester intermediates (e.g., a soluble carboxylate salt, such as tetraethylammonium acetate) is added to the reaction mixture. The compound (approximately 1.4 equiv.) can be added to the mixture of chiral ligand, water, solvent, oxidant and osmium catalyst and olefin, or prior to the addition of olefin, if the olefin slow-addition method is used.

Figure 4:
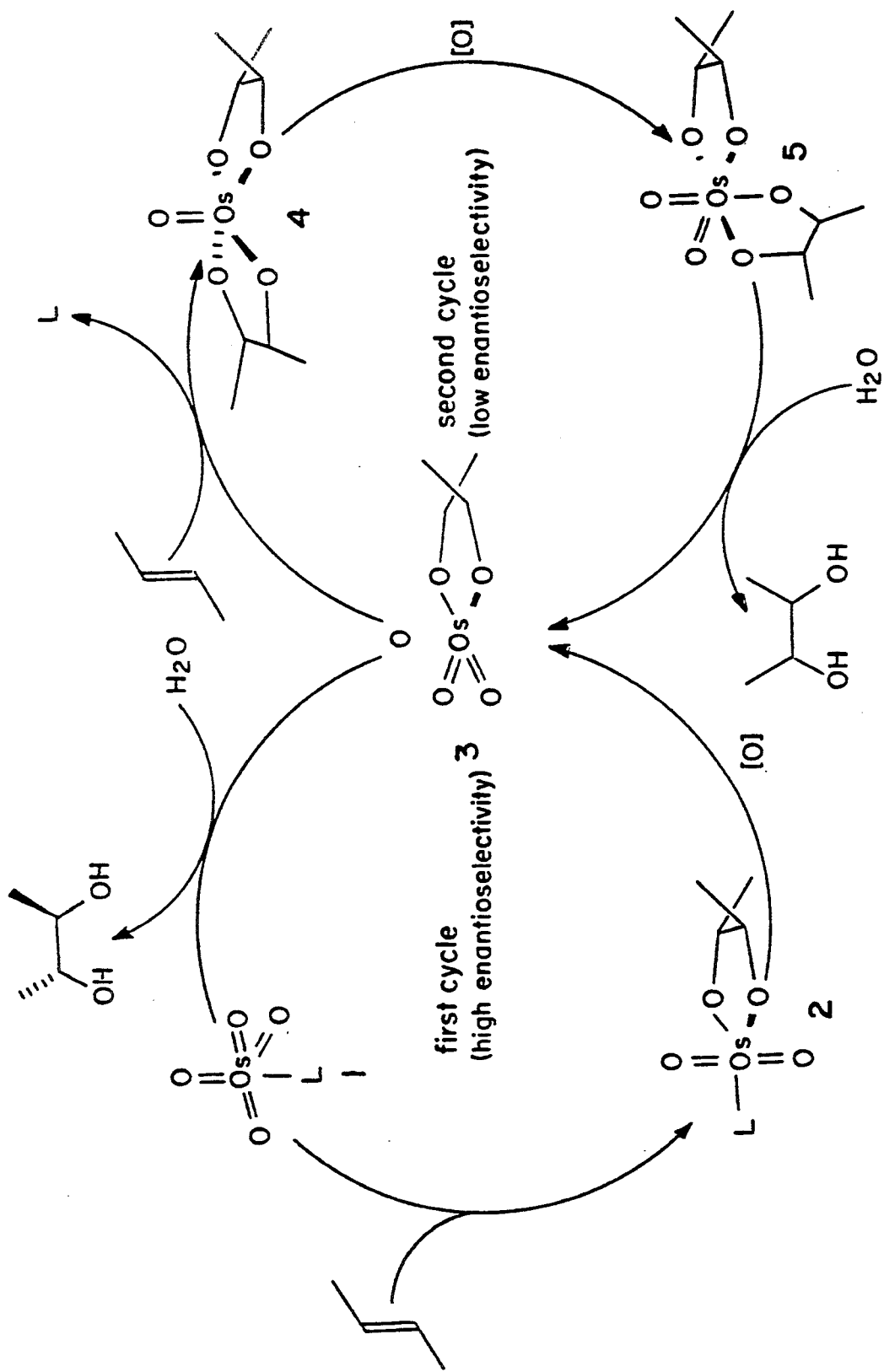
FIG. 4 is a schematic representation of a proposed mechanism catalytic olefin dihydroxylation. This scheme shows two diol-producing cycles believed to be involved in the ligand-accelerated catalysis of the present invention. Formula 1 represents an alkaloidosmium complex; formula 2 represents a monoglycolate ester; formula 3 represents an osmium(VIII)trioxoglycolate complex; formula 4 represents a bisglycolate osmium ester; and formula 5 represents a dioxobisglycolate.

The diol-producing mechanistic scheme which is thought to operate when the slow-addition of olefin method is used is represented in FIG. 4. According to the proposed mechanism at least two diol-producing cycles exist. As shown in FIG. 4 only the first cycle appears to result in high ee. The key intermediate is the osmium (VIII) trioxoglycolate complex, shown as formula 3 in FIG. 4, which has the following general formula:

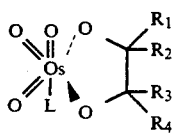

wherein L is a chiral ligand and wherein $R_1$, $R_2$, $R_3$ and $R_4$ are organic functional groups corresponding to the olefin. For example, $R_1$, $R_2$, $R_3$ and $R_4$ could be alkyl, aryl, alkoxy aryloxy or other organic functional groups compatible with the reaction process. Examples of olefins which can be used, and their functional groups are shown on Table 4 hereinabove.

This complex occupies the pivotal position at the junction between the two cycles, and determines how diol production is divided between the cycles.

Evidence in favor of the intermediacy of the osmium (VIII) trioxoglycolate complex (formula 3, FIG. 4) is provided by the finding that the events in FIG. 4 can be replicated by performing the process in a stepwise manner under stoichiometric conditions. These experiments were performed under anhydrous conditions in toluene. In the process shown in FIG. 4, one equivalent of the alkaloid osmium complex (shown as formula 1 FIG. 4) is allowed to react with an olefin to give the emerald green monoglycolate ester (formula 2, FIG. 4) A different olefin is then added, followed by an equivalent of an anhydrous amine N-oxide, and rapid formation of the bisglycolate ester (formula 4, FIG. 4) is observed. Upon reductive hydrolysis of the bisglycolate ester, precisely one equivalent of each diol is liberated. These experiments indicate that a second cycle, presumably via the osmium trioxoglycolate complex, is as efficient as the first in producing diols from olefins. One can also use the same olefin in both steps to run this tandem addition sequence. When this was done using 1.phenylcyclohexene as the olefin, the ee for the first step was 81% and the ee for the second step was 7% in the opposite direction (i.e., in favor of the minor enantiomer in the first step). Thus, for this substrate any intrusion of the second cycle is particularly damaging, and under the original catalytic conditions 1-phenylcyclohexene only gave 8% ee (entry 3, Table 5).

Reduced ee is just part of the counterproductivity of turning on the second cycle; reduced turnover is the other liability. The bisosmate esters (formula 4, FIG. 4) are usually slow to reoxidize and hydrolyze, and therefore tend to tie up the catalyst. For example, 1-phenylcyclohexene took 7 days to reach completion under the original conditions (the 8% ee cited above). With slow addition of the olefin, the oxidation was complete in one day and gave the diol in 95% yield and 78% ee (entry 3, Table 5).

The most important prediction arising from the mechanistic scheme shown in FIG. 4 is the minimization of the second cycle if the olefin is added slowly. Slow addition of the olefin presumably gives the osmium (VIII) trioxoglycolate intermediate sufficient time to hydrolyze so that the osmium catalyst does not get trapped into the second cycle by reacting with olefin. To reiterate, the second cycle not only ruins the ee but also impedes turnover, since some of the complexes involved are slow to reoxidize and/or hydrolyze. The optimum feed rate depends on the olefin; it can be determined empirically as described herein.

The maximum ee obtainable in the catalytic process is determined by the addition of the alkaloid osmium complex (formula 1, FIG. 4) to the olefin (i.e., the first column in Table 5). Thus, stoichiometric additions can be used to enable one to determine the ee-ceiling which can be reached or approached in the catalytic process if the hydrolysis of 3 (FIG. 4) can be made to dominate the alternative reaction with a second molecule of olefin to give 4 (FIG. 4). In the case of terminal olefins, styrene (Table 5), the trioxoglycolate esters hydrolyze rapidly, since slow addition, or the effect of the osmate ester hydrolytic additive give only a slight increase in the ee However, most olefins benefit greatly from any modification which speeds hydrolysis of the osmate ester intermediate (3, FIG. 4) (entries 2 5, Table 5), and in extreme cases neither the effect of the osmate ester-hydrolytic additive nor slow addition is sufficient alone. Diisopropyl ethylene (entry 4, Table 5) approaches its ceiling-ee only when both effects are used in concert, with slow addition carried out in the presence of acetate. The other entries in the Table reach their optimum ee's through slow addition alone, but even in these cases the addition times can be substantially shortened if a compound, such as a tetraalkyl ammonium acetate, is present.

In many cases, temperature also effects the ee. When the ee is reduced by the second cycle, raising the temperature can often increase it. For example, diisopropyl ethylene gave 46% ee at 0° C. and 59% ee at 25° C. (24h slow addition time in both cases). The rate of hydrolysis of the osmium trioxoglycolate intermediate is apparently more temperature dependent than the rate of its reaction with olefin. This temperature effect is easily rationalized by the expected need to dissociate the chiral ligand from the osmium complex (3) in order to ligate water and initiate hydrolysis, but the ligand need not dissociate for addition of olefin to occur (in fact this second cycle olefin addition step is also likely to be ligand-accelerated).

The following is a description of how optimum conditions for a particular olefin can be determined. To optimize the osmium-catalyzed asymmetric dihydroxylation: 1) If from the known examples there is doubt about what the ceiling-ee is likely to be, it can be determined by performing the stoichiometric osmylation in acetone/water at 0° C. using one equivalent of the OsO$_4$-alkaloid complex; 2) Slow addition at 0° C.: the last column in Table 3 can be used as a guide for choosing the addition time bearing in mind that at a given temperature each olefin has its own "fastest" addition rate, beyond which the ee suffers as the second cycle turns on. When the olefin addition rate is slow enough, the reaction mixture remains yellow-orange (color of 1, FIG. 4); when the rate is too fast, the solution takes on a blackish tint, indicating that the dark-brown-to-black bisglycolate complex (4, FIG. 4) is being generated; 3) If the ceiling ee is not reached after steps 1 and 2, slow addition plus tetraalkyl ammonium acetate (or other compound which assists hydrolysis of the osmate ester intermediate) at 0° C. can be used; 4) slow addition plus a soluble carboxylate salt, such as tetraalkyl ammonium acetate at room temperature can also be used. For all these variations, it is preferable that the mixtures is agitated (e.g., stirred) for the entire reaction period.

The method of the present invention can be carried out over a wide temperature range and the limits of that range will be determined, for example by the limit of the organic solvent used. The method can be carried out, for example, in a temperature range from about 40° C. to about −30° C. Concentrations of individual reactants (e.g., chiral ligand, oxidant, etc.) can be varied as the temperature at which the method of the present invention is carried out. The saturation point (e.g., the concentration of chiral ligand at which results are maximized) is temperature-dependant. As explained previously, for example, it is possible to reduce the amount of alkaloid used when the method is carried out at lower temperatures.

The organic solvent used in the present method can be, for example, acetone, acetonitrile, THF, DME, ethanol, methanol, pinacolone, tert butanol, toluene or a mixture of two or more organic solvents.

Figure 2:
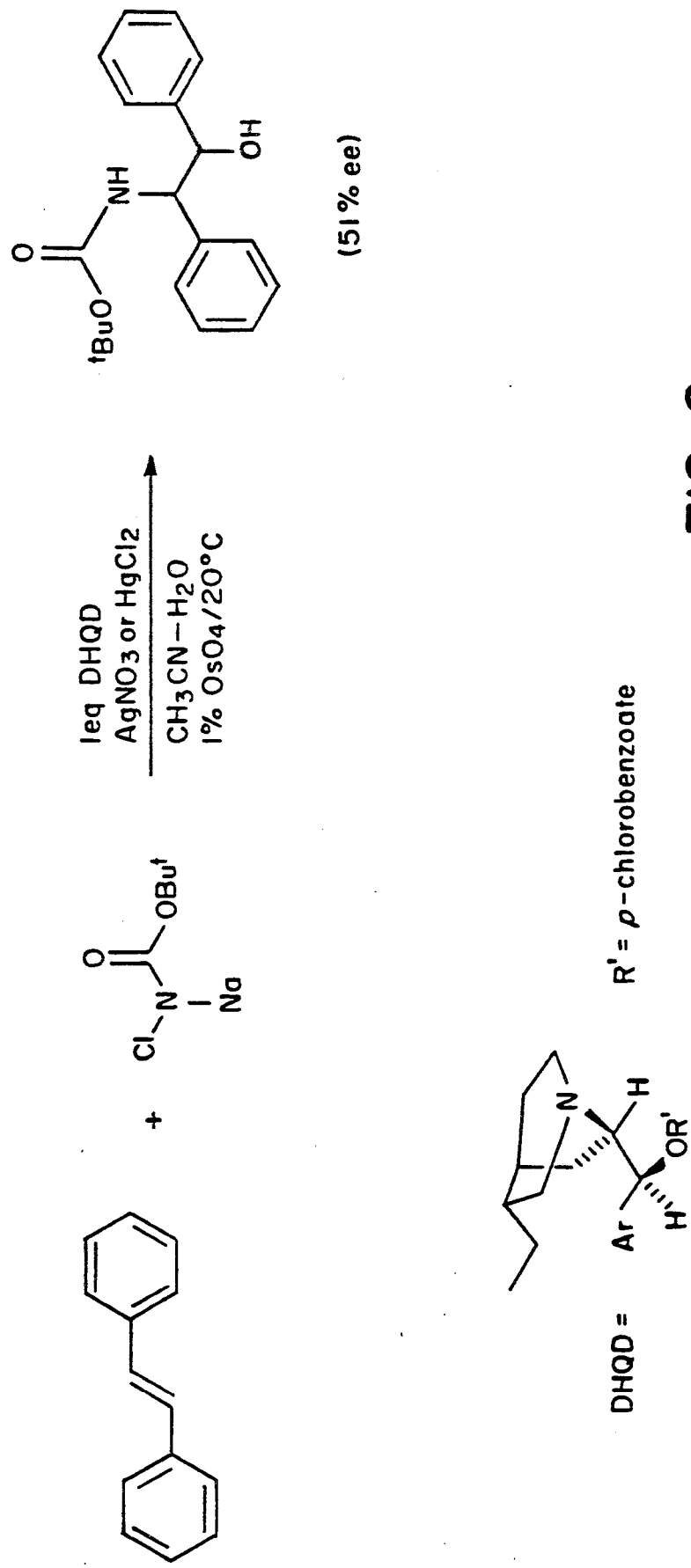
FIG. 2 is a schematic representation of asymmetric catalytic oxyamination of stilbene which is carried out by the method of the present invention.
Figure 3:
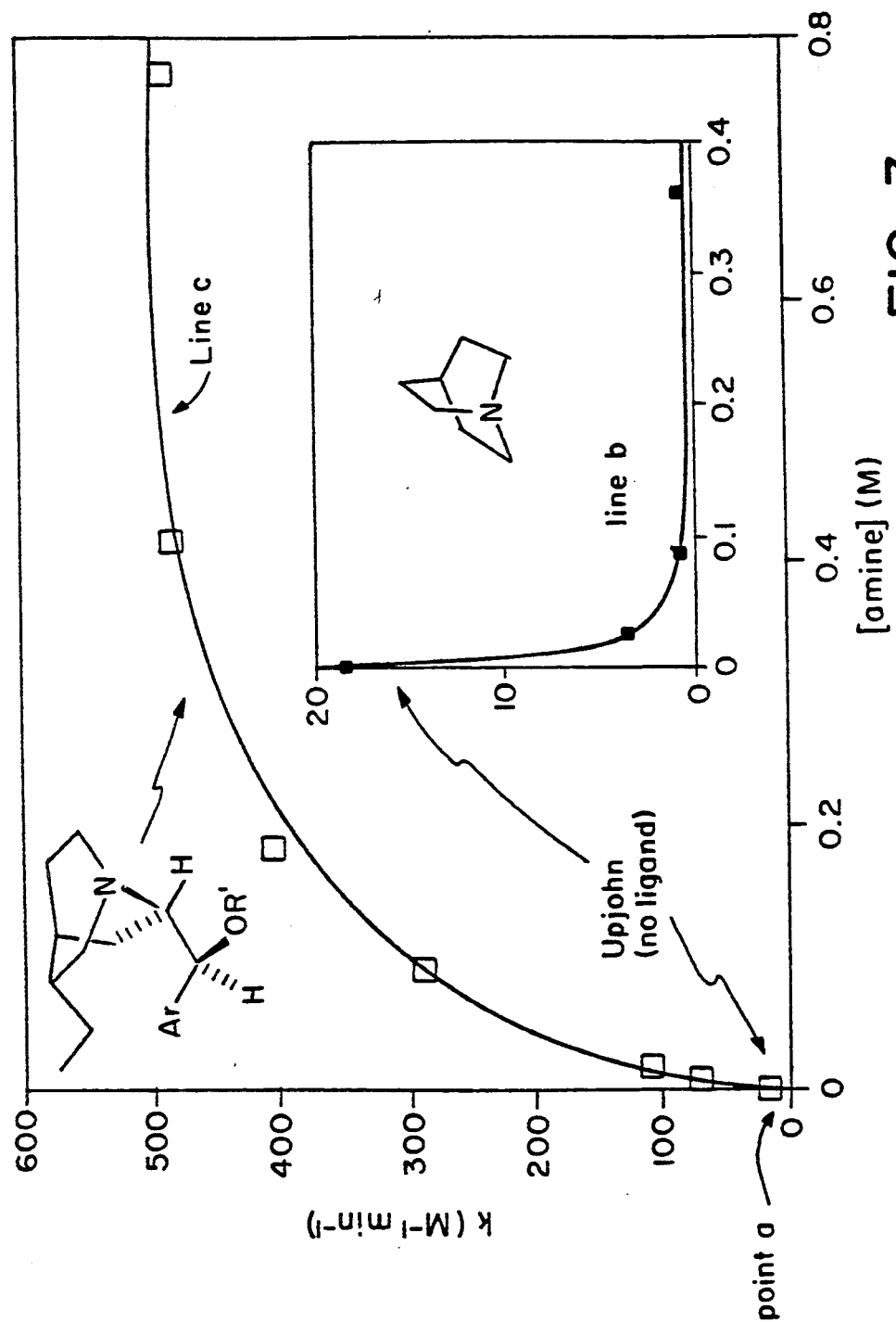
FIG. 3 is a plot of amine concentration vs second-order-rate constant k for the catalytic cis-dihydroxylation of styrene. At point a, no amine has been added. Point a thus represents the rate of the catalytic process in the absence of added amine ligands. Line b represents the rate of the catalytic process in the presence of varying amounts of quinuclidine, a ligand which substantially retards catalysis. Line c represents the rate of the catalytic process in the presence of the dihydroquinidine benzoate derivative 1 represented in FIG. 1. K is defined as $K_{obs}/[OsO_4]_o$ where rate= $-d[styrene]/dt$ = $K_{obs}$ [styrene]. Conditions: 25° C., $[OsO_4]_o = 4 \times 10^{-4}$M, $[NMO]_o -0.2$M $[styrene]_o = 0.1$M.

In another embodiment of the present invention, styrene was combined with a chiral ligand (DHQD), acetone water and NMO and OsO4. The plot of amine concentration vs second-order-rate-constant K for the catalytic cis-dihydroxylation of styrene is represented in FIG. 2. The kinetic data of FIG. 2 clearly shows the dramatic effect of ligand-accelerated catalysis achieved by use of the method of the present invention. Point a in FIG. 2 represents the rate of the catalytic process in the absence of amine ligands (t1/2=108 minutes). Line b shows the rates of the process in the presence of varying amounts of quinuclidine, a ligand which substantially retards catalysis (at greater than 0.1M quinuclidine, t1/2 is greater than 30 hours). Because of the observed retarding effect of quinuclidine (ligand-decelerated catalysis) the result represented by line C was unexpected. That is, when the process occurs in the presence of dihydroquinidine benzoate derivative 1 (see FIG. 1), the alkaloid moiety strongly accelerates the catalytic process at all concentrations (with ligand 1=0.4M, t1/2=4.5 minutes), despite the presence of the quinuclidine moiety in its structure.

The rate of the stoichiometric reaction of styrene with osmium tetroxide and that of the corresponding catalytic process were compared. The comparison indicates that both have identical rate constants [$K_{stoic}=(5.1\pm0.1)\times10^2 M^{-1}$ min$^{-1}$ and $K_{cat}=(4.9\pm0.4)\times10^2 M^{-1}$ min$^{-1}$], and that they undergo the same rate acceleration upon addition of ligand 1. Hydrolysis and reoxidation of the reduced osmium species, steps which accomplish catalyst turnover, are not kinetically significant in the catalytic process with styrene. It may be concluded that the limiting step is the same in both processes and consists of the initial addition reaction forming the osmate ester (2, FIG. 1) A detailed mechanistic study reveals that the observed rate acceleration by added ligand 1 is due to formation of an osmium tetroxide-alkaloid complex which, in the case of styrene, is 23 times more reactive than free osmium tetroxide. The rate reaches a maximal and constant value beyond an (approximate) 0.25M concentration of ligand 1. The onset of this rate saturation corresponds to a pre-equilibrium between DHQD and osmium tetroxide with a rather weak binding constant ($K_{eq}=18\pm2M^{-1}$). Increasing the concentration of DHQD above 0.25M does not result in corresponding increases in the enantiomeric excess of the product diol. In fact, due to the ligand-acceleration effect, the ee of the process approaches its maximum value much faster than the maximum rate is reached, which means that optimum ee can be achieved at rather low alkaloid concentrations.

At least in the case of styrene, the rate acceleration in the presence of the alkaloid is accounted for by facilitation of the initial osmylation step. The strikingly opposite effects of quinuclidine and DHQD on the catalysis can be related to the fact that although quinuclidine also accelerates the addition of osmium tetroxide to olefins, it binds too strongly to the resulting osmium(VI) ester intermediate and inhibits catalyst turnover by retarding the hydrolysis/reoxidation steps of the cycle. In contrast the alkaloid appears to achieve a balancing act which renders it near perfect for its role as an accelerator of the dihydroxylation catalysis. It binds strongly enough to accelerate addition to olefins, but not so tightly that it interferes (as does quinuclidine) with subsequent stages of the catalytic cycle. Chelating tertiary amines [e.g., 2,2'-bipyridine and (−)-(R,R)—N,N,N',N'-tetramethyl-1,2-cyclohexanediamine) at 0.2M completely inhibit the catalysis. Pyridine at 0.2M has the same effect.

As represented in Table 4 the method of the present invention has been applied to a variety of olefins. In each case, the face selection rule described above has been shown to apply (with reference to the orientation of the olefin as represented in FIG. 1). That is, in the case of the asymmetric dihydroxylation reaction in which the dihydroquinidine derivative is the chiral ligand, attack occurs on the re- or re,re- face) and in the case in which the dihydroquinine derivative is the chiral ligand, attack occurs on the si or si,si- face. Thus, as demonstrated by the data presented in the Table 2, the method of the present invention is effective in bringing about catalytic asymmetric dihydroxylation; in all cases, the yield of the diol was 80–95%, and with the slow-addition modification, most olefins give ee's in the rage of 40–90%.

The present method can be used to synthesize chiral intermediates which are important building blocks for biologically active chiral molecules, such as drugs. In one embodiment, the present method was used to produce an optically pure intermediate used in synthesizing the drug diltiazum (also known as cardizem). The reaction is shown in the following scheme:

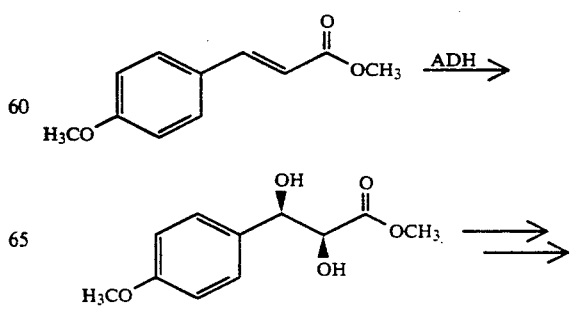

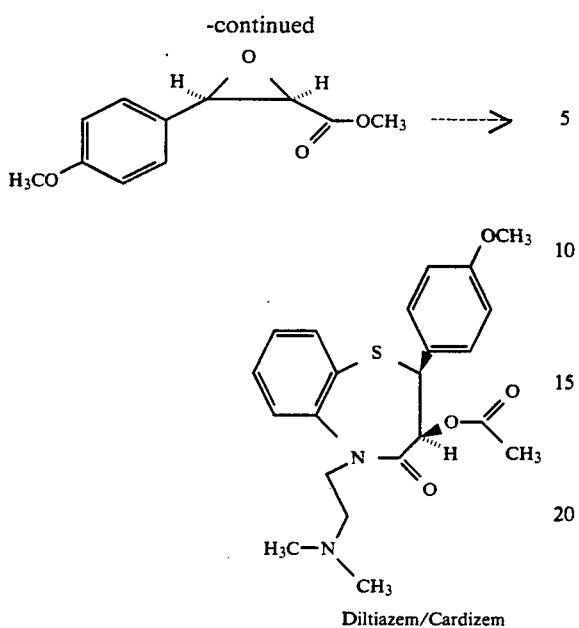

Diltiazem/Cardizem

The method of the present invention is also useful to effect asymmetric vicinal oxyamination of an olefin, and may be useful for asymmetric vicinal diamination. In the case of substitution of two nitrogen or of a nitrogen and oxygen, an amino derivative is used as an amino transfer agent and as an oxidant. For example, the olefin to be modified, an organic solvent, water, a chiral ligand, an amino derivative and an osmium, containing compound are combined and the combination maintained under conditions appropriate for the reaction to occur. The amino derivative can be, for example, an N-chlorocarbamate or chloroamine T. Asymmetric catalytic oxyamination of recrystallized trans stilbene, according to the method of the present invention, is represented in FIG. 2.

In another embodiment, the present method was used to produce intermediates for the synthesis of homo-brassinolide and 24-epibrassinolide, which are known to exhibit the same biological activities as brassinolide. These brassinosteroids show very potent plant-growth activity at hormonal level and access to these compounds in a large quantity can only be achieved by synthetic means.

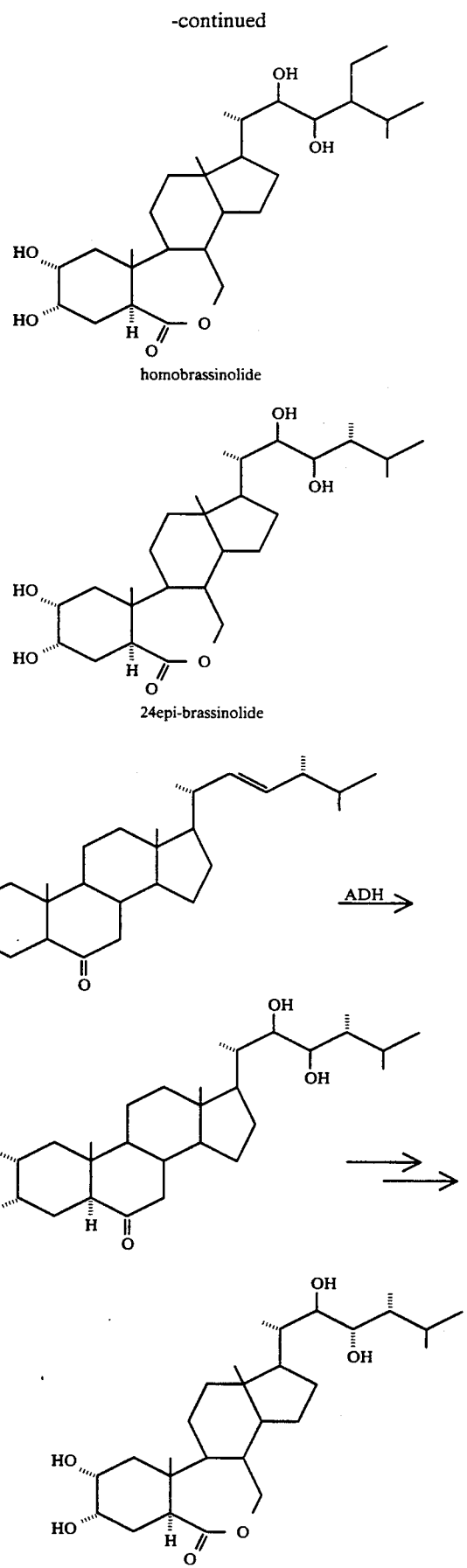

In another embodiment of the present method, highly optically active diol was produced from the asymmetric dihydroxylation of ethyl trans-2-octenoate. This diol can then be easily converted to optically pure β-lactam structure, which are well-known for their antibiotic activities:

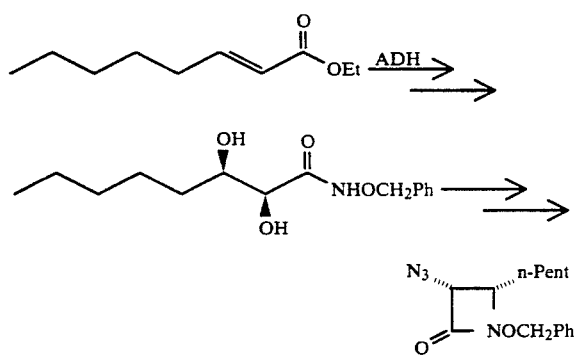

EXAMPLE I Asymmetric Dihydroxylation of Stilbene.

The following were placed sequentially in a 2L bottle (or flask): 180.2 g (1.0M) of recrystallised trans stilbene (Aldrich 96%), 62.4 g (0.134 moles; 0.134 eq) of the p-chlorobenzoate of hydroquinidine (1), 450 mL of acetone, 86 mL of water (the solution is 0.261M in alkaloid 1) and 187.2 g (1.6 mol, 1.6 eq.) of solid N-Methylmorpholine N-Oxide (NMO, Aldrich 97%). The bottle was capped, shaken for 30 seconds, cooled to 0.4° C. using an ice-water bath. $OsO_4$ (4.25 mL of a solution prepared using 0.120 g $OsO_4$/mL toluene; 0.002 Mol%; 0.002 eq.) was injected. The bottle was shaken and placed in a refrigerator at ca. 4° C. with occasional shaking. A dark purple color developed and was slowly replaced by a deep orange one; the heterogeneous reaction mixture gradually became homogeneous and at the end of the reaction, a clear orange solution was obtained. The reaction can be conveniently monitored by TLC (silica gel; $CH_2Cl_2$; disappearance of the starting material at a defined Rf). After 17 hours, 100 g of solid sodium metabisulfite ($Na_2S_2O_5$) were added, the reaction mixture was shaken (1 minute) and left at 20° C. during 15 minutes. The reaction mixture was then diluted by an equal volume of $CH_2Cl_2$ and anhydrous $Na_2SO_4$ added (100 g). After another 15 minutes, the solids were removed by filtration through a pad of celite, washed three times with 250 mL portions of $CH_2Cl_2$ and the solvent was evaporated under vacuum (rotatory-evaporator, bath temperature = 30°-35° C.).

The crude oil was dissolved in ethyl acetate (750 mL), extracted three times with 500 ml. portions of 2.0M HCl, once with 2.0M NaOH, dried over $Na_2SO_4$ and concentrated in vacuo to leave 190 g (89%) of the crude diol as a pale yellow solid. The enantiomeric excess of the crude R,R-diol was determined to be 78% by HPLC analysis of the derived bis-acetate (Pirkle 1A column using 5% isopropanol/hexane mixture as eluant. Retention times are: t1 = 18.9 minutes; t2 = 19.7 minutes. Recrystallization from about 1000 ml. $CH_2Cl_2$ gave 150 g (70%) of pure diol (ee = 90%). A second recrystallization gave 115 g of diol (55% yield) of 99% ee. Ee (enantiomeric excess) is calculated from the relationship (for the R enantiomer, for example): percent $e.e. = [(R)-(S)/[(R)+(S)] \times 100$.

The aqueous layer was cooled to 0° C. and treated with 2.0M NaOH (about 500 mL) until pH = 7. Methylene chloride was added (500 mL) and the pH adjusted to 10-11 using more 2.0M NaOH (about 500 mL). The aqueous layer was separated, extracted twice with methylene chloride (2×300 mL) and the combined organic layers were dried over $Na_2SO_4$. The solvent was removed in vacuo to provide the alkaloid as a yellow foam. The crude alkaloid was dissolved in ether (1000 mL), cooled to 0° C. (ice-bath) and treated with dry HCl until acidic pH (about 1 2). The faint yellow precipitate of p-chlorobenzoylhydroquinidine hydrochloride was collected by filtration and dried under high vacuum (0.01 mm Hg).

The free base was liberated by suspending the salt in ethyl acetate (500 mL), cooling to 0° C. and adding 28% $NH_4OH$ until pH = 11 was reached. After separation, the aqueous layer was extracted twice with ethyl acetate, the combined organic layers were dried over $Na_2SO_4$ and the solvent removed in vacuo to give the free base as a white foam.

EXAMPLE 2 Asymmetric Dihydroxylation of Stilbene

To a 3 L, 3-necked, round-bottomed flask equipped with a mechanical stirrer and two glass stoppers at room temperature were added E-1,2-diphenylethene (Trans-stilbene) (180.25 g, 1.0 mol, 1.0 eq). 4-methylmorpholine N-oxide (260 mL of a 60% by wt. aqueous solution (1.5 mol, 1.5 eq) dihydroquinidine 4-chlorobenzoate (23.25 g, 0.05 mol, 0.05 eq) 375 mL acetone and 7.5 mL $H_2O$. The solution was 0.1M in alkaloid M in olefin, and the solvent was 25% water/75% acetone (v/v). The flask was immersed in a 0° C. cooling bath and stirred for 1 h. Osmium tetroxide (1.0 g, 4.0 mmol., 4.0×10.3 eq) was added in one portion producing a milky brown-yellow suspension. The reaction mixture was then stirred at 0° C. for 24 h and monitored by silica TLC (3:1 $CH_2Cl_2$:$Et_2O$ v/v). At this point, sodium metabisulfite (285 g, 1.5 mol) was added, the mixture was diluted with 500 mL of $CH_2Cl_2$, warmed to room temperature, and stirred at room temperature for 1 h. Anhydrous sodium sulfate (50 g) was added and the mixture was stirred at room temperature overnight. The suspension was filtered through a 20 cm Buchner funnel, the filtrand was rinsed thoroughly with acetone (3×250 mL), and the filtrate was concentrated to a brown paste on a rotary evaporator with slight heating (bath temperature 30°-40° C.). The paste was dissolved in 3.5 L of EtOAc, transferred to a 6 L separatory funnel, and washed sequentially with $H_2O$ (2×500 mL). and brine (1×500 mL). The initial aqueous washes were kept separate from the subsequent acid washes which were retained for alkaloid recovery. The organic layer was dried ($Na_2SO_4$), and concentrated to give the crude diol in quantitative yield (222.7 g, 1.04 mol, 104%). The ee of the crude product was determined by $^1H$ NMR analysis of the derived bis-Mosher ester to be 90%. One recrystallization from hot 95% aqueous ethanol (3 mL/g) afforded 172-180 g (80-84%) of enantiomerically pure stilbene diol as a white solid, mp 145.5°-146.5° C., $[\alpha]_D^{25} = 91.1°$ (c = 1.209, abs EtOH).

EXAMPLE 3 Asymmetric Dihydroxylation of Stilbene

Asymmetric dihydroxylation of stilbene was carried out as described in Example 1, except that 1.2 equivalents of NMO were used.

EXAMPLE 4 Asymmetric Dihydroxylation of Stilbene

Asymmetric dihydroxylation of stilbene was carried out as described in Example 1, except that 1.2 equivalents of NMO, as a 62% wt. solution in water, were used.

EXAMPLE 5 Preparation of Dihydroquinidine by Catalytic

Preparation of Dihydroquinidine by Catalytic Reduction of Quinidine

To a solution of 16.2 g of quinidine (0.05 mol) in 150 mL of 10% $H_2SO_4$ (15 g conc $H_2SO_4$ in 150 mL $H_2O$) was added 0.2 g of $PdCl_2$ (0.022 eq; 0.0011 mol). The reaction mixture was hydrogenated in a Parr shaker at 50 psi pressure. After 2 h, the catalyst was removed by filtration through a pad of celite and washed with 150 mL of water. The faint yellow solution so obtained was slowly added to a stirred aqueous NaOH solution (15 g of NaOH in 150 mL $H_2O$. A white precipitate immediately formed and the pH of the solution was brought to 10–11 by addition of excess aqueous 15% NaOH. The precipitate was collected by filtration, pressed dry and suspended in ethanol (175 mL). The boiling solution was quickly filtered and upon cooling to room temperature, white needles crystallized out. The crystals were collected and dried under vacuum (90° C.; 0.05 mm Hg) overnight. This gave 8.6 g (52.7%) of pure dihydroquinidine mp=169.5°–170° C. The mother liquor was placed in a freezer at 15° C. overnight. After filtration and drying of the crystals, another 4.2 g (21.4%) of pure material was obtained, raising the total amount of dihydroquinidine to 12.8 g (74.1%).

Preparation of dihydroquinidine p-chlorobenzoate (ligand 1)

From dihydroquinidine hydrochloride (Aldrich)

To a cooled (0° C.) suspension of 100 g dihydroquinidine hydrochloride (0.275 mol) in 300 mL of dry $CH_2Cl_2$ was added, over 30 minutes with efficient stirring, 115 mL of $Et_3N$ (0.826 eq; 3 eqs) dissolved in 50 mL of $CH_2Cl_2$. The dropping funnel was rinsed with an additional 20 mL of $CH_2Cl_2$. After stirring 30 minutes at 0° C., 42mL of p-chlorobenzoyl chloride (0.33 mol;57.8 g; 1.2 eq) dissolved in 120 mL of $CH_2Cl_2$ was added dropwise over a period of 2 h. The heterogeneous reaction mixture was then stirred 30 minutes at 0° C. and 1 hour at room temperature; 700 mL of a 3.0M NaOH solution was then slowly added until pH=10–11 was obtained. After partitioning the aqueous layer was extracted with three 100 mL portions of $CH_2Cl_2$. The combined organic layers were dried over $Na_2SO_4$ and the solvent removed in vacuo (rotatory evaporator). The crude oil was dissolved in 1 L of ether, cooled to 0° C. and treated with HCl gas until the ether solution gives a pH of about 2 using wet pH paper. The slightly yellow precipitate was collected and dried under vacuum to give 126 g (91.5%) of dihydroquinidine p-chlorobenzoate hydrochloride.

The salt was suspended in 500 mL of ethyl acetate, cooled to 0° C. and treated with 28% $NH_4OH$ until pH=11 was reached. After separation, the aqueous layer was extracted with two 200 mL portions of ethyl acetate. The combined organic layers were dried over $Na_2SO_4$ and the solvent removed under vacuum, leaving the free base 1 as a white foam (112 g; 88% overall). This material can be used without further purification, or it can be recrystallized from a minimum volume of hot acetonitrile to give an approximately 70–80% recovery of colorless crystals: mp: 102°–104° C., $[]^{25}D$-76.5° [c1.11, EtOH); IR ($CH_2Cl_2$) 2940, 2860, 1720, 1620, 1595, 1520, 1115, 1105, 1095, 1020 cm$^{-1}$; $^1H$ NMR ($CDCl_3$) 8.72 (d, 1H, J-5 Hz), 8.05 (br d, 3H, J=9.7 Hz), 7.4 (m, 5H), 6.72 (d, 1H, J=7.2 Hz), 3.97 (s, 3H), 3.42 (dd, 1H, J=9, 19.5 Hz), 2.9–2 7 (m, 4H), 1.87 (m, 1H), 1.75 (br s, 1H), 1.6–1.45 (m, 6H), 0.92 (t, 3H, J=7 Hz). Anal. Calcd for $C_{27}H_{29}ClN_2O_3$ C, 69.74; H, 6.28; Cl, 7.62; N, 6.02. Found: C, 69.95;H, 6.23; Cl, 7.81; N, 5.95.

From dihydroquinidine

To a 0° C. solution of 1.22 g dihydroquinidine (0.0037 mol) in 30 mL of $CH_2Cl_2$ was added 0.78 mL of $Et_3N$ (0.0056 mol; 1.5 eq). followed by 0.71 mL of p-chlorobenzoyl chloride (0.005 mol; 1.2 eq) in 1 mL $CH_2Cl_2$. After stirring 30 minutes at 0° C. and 1 hour at room temperature, the reaction was quenched by the addition of 10% $Na_2CO_3$ (20 mL). After separation, the aqueous layer was extracted with three 10 mL portions of $CH_2Cl_2$. The combined organic layers were dried over $Na_2SO_4$ and the solvent removed under vacuum. The crude product was purified as described above. Dihydroquinidine p-chlorobenzoate (1) was obtained in 91% yield (1.5 g) as a white foam.

Recovery of dihydroquinidine p-chlorobenzoate

The aqueous acidic extracts (see EXAMPLE 1) were combined, cooled to 0° C. and treated with 2.0M NaOH solution (500 mL) until pH=7 was obtained. Methylene chloride was added (500 mL) and the pH was adjusted to 10–11 using more 2.0M NaOH. The aqueous layer was separated and extracted with two 300 mL portions of $CH_2Cl_2$. The combined organic layers were dried over $Na_2SO_4$ and concentrated to leave the crude alkaloid as a yellow foam. The crude dihydroquinidine p-chlorobenzoate (1) was dissolved in 1L of ether, cooled to 0° C. and HCl gas was bubbled into the solution until a pH of 1–2 was obtained using wet pH paper. The pale yellow precipitate of 1 as the hydrochloride salt was collected by filtration and dried under high vacuum (0.01 mm Hg). The free base was liberated by suspending the salt in 500 mL of ethyl acetate, cooling the heterogeneous mixture to 0° C. and adding 28% $NH_4OH$ (or 15% NaOH) until pH=11 was obtained. After separation, the aqueous layer was extracted with two 100 mL portions of ethyl acetate the combined organic layers were dried over $Na_2SO_4$ and the solvent removed in vacuo to give 56g (91% recovery) of pure dihydroquinidine p-chlorobenzoate (1) as a white foam.

EXAMPLE 6 Preparation of Dihydroquinine Derivative

Preparation of dihydroquinine p-chlorobenzoate

The catalytic hydrogenation and p-chlorobenzoylation were conducted as described for the dihydroquinidine p-chlorobenzoate to give a white amorphous solid in 85.90% yield. This solid can be used without further purification, or it can be recrystallized from a minimum volume of hot acetonitrile to afford colorless crystals: Mp: 130°–133° C. $[a]^{25}D+150°$ (c 1.0, EtOH). The physical properties of the solid before recrystallization (i.e., the "white amorphous solid") are as follows: [ $]^{\alpha D}+142.1$ (C=1, EtOH); IR ($CH_2Cl_2$) 2940, 2860, 1720, 1620, 1595, 1508, 1115, 1105, 1095, 1020 cm$^{-1}$, $^1H$ NMR (CDCl$_3$) d 8.72 (d, 1H, J=5 Hz), 8.05 (br d, 3H, J=8 Hz), 7.4 (m, 5H), 6.7 (d, 1H, J=8 Hz), 4.0 (s. 3H), 3.48 (dd, 1H, J=8.5, 15.8 Hz), 3.19 (m, 1H), 3.08 (dd, 1H, J=11, 15 Hz), 2.69 (ddd, 1H, J=5, 12, 15.8 Hz), 2.4 (dt, 1H, J=2.4, 15.8 Hz). 1.85–1.3 (m, 8H), 0.87 (t, 3H, J=Hz). Anal. Calcd for C$_{27}$H$_{29}$ClN$_2$O$_3$; C, 69.74; H, 6.28; Cl, 7.62; N, 6.02. Found: C. 69.85; H. 6.42; Cl, 7.82; N, 5.98.

Recovery of dihydroquinine p-chlorobenzoate (2) ·

The procedure is identical to that described above for recovery of 1.

EXAMPLE 7 Procedure for Asymmetric Dihydroxylation of Trans-3-hexene Under "Slow Addition" Conditions To a well stirred mixture of 0.465g (1 mmol, 0.25 eq-0.25M in L) dihydroquinidine 4-chlorobenzoate (Aldrich. 98%), 0.7 g (6 mmol. 1.5 eq) N-methylmorpholine N-oxide (Aldrich, 97%). and 32 L of a 0.5M toluene solution of osmium tetroxide (16 mol, 4×10$^{-3}$ equiv), in 4 mL of an acetone-water mixture (10:1 v/v) at 0° C., neat 0.5 mL (0.34 g, 4 mmol) trans-3-hexene (Wiley, 99.9%) was added slowly, via a gas tight syringe controlled by a syringe pump and with the tip of the syringe needle immersed in the reaction mixture, over a period of 16 h. The mixture gradually changed from heterogeneous to homogeneous. After the addition was complete, the resulting clear orange solution was stirred at 0° C. for an additional hour. Solid sodium metabisulfite (Na$_2$S$_2$O$_5$, 1.2 g) was added and the mixture was stirred for 5 min. and then diluted with dichloromethane (8mL) and dried (Na$_2$SO$_4$). The solids were removed by filtration, and washed three times with dichloromethane. The combined filtrates were concentrated, and the residual oil was subjected to flash column chromatography on silica gel (25 g, elution with diethyl ether-dichloromethane, 2:3 v/v, R$_f$0.33) and collection of the appropriate fractions afforded 0.30–0.32 g (85.92% yield) of the hexanediol. The enantiomeric excess of the diol was determined by GLC analysis (5% phenyl-methylsilicone, 0.25 m film, 0317 mm diameter, 29 m long) of the derived bis-Mosher ester to be 70%.

When the above reaction was repeated with 1.2 mL (6mmol, 1.5eq) 60% aqueous NMO (Aldrich) in 4 mL acetone, an ee of 71% was obtained. Thus, this aqueous NMO gives equivalent results and is almost twenty times less expensive than the 97% solid grade. With an alkaloid concentration of only 0.1M (i.e., 0.186 g) and with an olefin addition period of 20 hours at 0° C., the ee was 65%. A small sacrifice in ee thus leads to a large saving in alkaloid. At 0° C., both trans 3-hexene and trans-methylstyrene reach their maximum ee value between 0.20 and 0.25M alkaloid concentration.

EXAMPLE 8 Asymmetric Dihydroxylation of 1-Phenylcyclohexene with Et$_4$NOAc-4H$_2$O The procedure set out in EXAMPLE 1 was followed, except that 1-phenylcyclohexene (1.0M) was substituted for trans-stilbene. The reaction was allowed to proceed for three days, after which only 40% conversion to the diol was obtained (8% ee).

The above procedure was repeated, with the difference that 2 equivalents of tetraethyl ammonium acetate (Et$_4$NOAc-4H$_2$O) was added to the reaction mixture at the beginning of the reaction. Fifty-two (52%) percent ee was obtained using this procedure, and the reaction was finished in about one day.

EXAMPLE 9 Asymmetric Dihydroxylation of trans-Stilbene under "phase-transfer" conditions in toluene To a well-stirred mixture of 58.2 mg (0.125 mmol; 0.25 eq.) of the p-chlorobenzoate of hydroquinidine, 1 mL of toluene, 88 mg (0.75 mmol; 1.5 eq.) of N-methylmorpholine N-oxide, 181 mg (1 mmol; 2 eq.) of tetramethylammonium hydroxide pentahydrate, 57 μL (2 mmol; 2 eq.) of acetic acid, 0.1 mL of water. and OsO$_4$ (4.2 μL of solution prepared using 121 mg OsO$_4$/mL toluene; 0.004 Mol %, 0.004 eq ) at room temperature, a toluene solution (1 mL) of 90 mg (0.4 mmol) of trans stilbene was added slowly, with a gas-tight syringe controlled by a syringe pump and with the tip of the syringe needle immersed in the reaction mixture, over a period of 24 h. After the addition was completed, 10% NaHSO$_3$ solution (2.5 mL) was added to the mixture, and the resulting mixture was stirred for 1 h. Organic materials were extracted with ethyl acetate, and the combined extracts were washed with brine and dried over Na2SO$_4$. The solvent was evaporated under reduced pressure, and the residual oil was subjected to column chromatography on silica gel (5 g, elution with hexane-ethyl acetate, 2:1 v/v. R$_f$0.17) to afford 67.3 mg (63%) of the diol. The enantiomeric excess of the diol was determined by HPLC analysis of the derived bis-acetate (Pirkle 1A column using 5% isopropanol/hexane mixture as eluant. Retention times are: t$_1$=22.6 minutes; t$_2$=23.4 minutes) to be 94%.

EXAMPLE 10 Asymmetric Dihydroxylation of trans-Methyl 4-methoxycinnamate under phase-transfer conditions in toluene To a well stirred mixture of 116.3 mg (0.25 eq.) of the p-chlorobenzoate of hydroquinidine, 2 mL of toluene, 175.8 mg (1.5 mmol; 1.5 eq.) of N-methylmorpholine N-oxide, 522 mg (2 mmol; 2 eq.) of tetraethylammonium acetate tetrahydrate, 0.2 mL of water, and OsO$_4$ (8.4 μL of solution prepared using 121 mg OsO$_4$/mL toluene; 0.004 Mol %, 0.004 eq.) at room temperature, a toluene solution (1 mL) of 192 mg (1 mmol) of trans-methyl 4-methoxycinnamate was added slowly, with a gas-tight syringe controlled by a syringe pump and with the tip of the syringe needle immersed in the reaction mixture, over a period of 24 h. After the addition was complete, 10% NaHSO$_3$ solution (5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (10 g, elution with hexane-ethyl acetate, 2:1 v/v R$_f$0.09) to afford 118 8 mg (53%) of the diol. The enantiomeric excess of the diol was determined by HPLC analysis of the derived bis-acetate (Pirkle Covalent Phenyl Glycine column using 10% isopropanol/hexane mixture as eluant. Retention times are: t$_1$=25.9 minutes; t$_2$=26.7 minutes) to be 84%.

EXAMPLE 11 Asymmetric Dihydroxylation of trans-Stilbene in the presence of Boric Acid To a well-stirred mixture of 58.2 mg (0.125 mmol; 0.25 eq) of the p-chlorobenzoate of hydroquinidine, 70 mg (0.6 mmol; 1.2 eq.) of N-methylmorpholine N-oxide, 37 mg (0.6 mmol; 1.2 eq.) of boric acid, 0.5 mL of dichloromethane, and OsO$_4$ (4.2 μL of a solution prepared using 121 mg OsO$_4$/mL toluene; 0.004 Mol %, 0.004 eq.) at room temperature, a dichloromethane solution (1 mL) of 90 mg (0.5 mmol) of trans-stilbene was added slowly, with a gas-tight syringe controlled by a syringe pump and with the tip of the syringe needle immersed in the reaction mixture, over a period of 24 h. After the addition was complete, 10% NaHSO$_3$ solution (2.5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (5 g. elution with hexane, ethyl acetate, 2:1 v/v, R$_f$0.17) to afford 78.3 mg (73%) of the diol. The enantiomeric excess of the diol was determined by $^1$H-NMR (solvent: CDCl$_3$) analysis of the derived bis-Mosher ester to be 94%.

EXAMPLE 12 Asymmetric Dihydroxylation of trans-Methyl 4-methoxycinnamate in the presence of Boric Acid To a well-stirred mixture of 116.3 mg (0.25 mmol; 0.25 eq ) of the p-chlorobenzoate of hydroquinidine, 175.8 mg (1.5 mmol; 1.5 eq.) of N-methylmorpholine N-oxide, 74.4 mg (1.2 mmol; 1.2 eq.) of boric acid, 1 mL of dichloromethane, and OsO$_4$ (8.4 μL of a solution prepared using 121 mg OsO$_4$/mL toluene, 0.004 mol %, 0.004 eq.) at room temperature, a dichloromethane solution (1 mL) of 192 mg (1 mmol) of trans-methyl 4-methoxycinnamate was added slowly, with a gas-tight syringe controlled by a syringe pump and with the tip of the syringe needle immersed in the reaction mixture, over a period of 24 h. After the addition was complete, 10% NaHSO$_3$ solution (5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure, and the residual oil was subjected to column chromatography on silica gel (10 g, elution with hexane-ethyl acetate, 2:1 v/v, R$_f$0.09) to afford 151 1 mg (67%) of the diol. The enantiomeric excess of the diol was determined by HPLC analysis of the derived bis-acetate (Pirkle Covalent Phenyl Glycine column using 10% isopropanol/hexane mixture as eluant. Retention times are: t$_1$=24.0 minutes; t$_2$=24.7 minutes) to be 76%.

EXAMPLE 13 Asymmetric Dihydroxylation of trans-β-Methylstyrene in the presence of Boric Acid To well-stirred mixture of 58.2 mg (0.125 mmol; 0.25 eq) of the p-chlorobenzoate of hydroquinidine, 70 mg (0.6 mmol; 1.2 eq) of N-methylmorpholine N-oxide, 72 mg (0.6 mmol; 1.2 eq) of phenylboric acid, 0.5 mL of dichloromethane, and OsO$_4$ (4.2 μL [of a solution prepared using 121 mg OsO$_4$/mL toluene; 0.004 Mol %, 0.004 eq) at 0° C., a dichloromethane solution] (0.5 mL), 65 μL (0.5 mmol) trans-β-methylstyrene was added slowly, with a gas-tight syringe controlled by a syringe pump and with the tip of the syringe needle immersed in the reaction mixture, over a period of 24 h. After the addition was complete, 10% NaHSO$_3$ solution (2.5 mL) was added to the mixture, and the resulting mixture was stirred for 1 h. Organic materials were extracted with ethyl acetate, and the combined extracts were washed with brine and dried over Na$_2$SO$_4$. The solvent was evaporated under reduced pressure and the residual oil was subjected to column chromatography on silica gel (5 g. elution with hexaneethyl acetate, 2:1 v/v, R$_f$0.62) to afford 109 mg (91%) of the phenylborate. The phenylborate was dissolved into acetone (3 mL) and 1,3-propandiol (0.5 mL), and the resulting mixture was stood for 2 h at room temperature. The solvent was evaported under reduced pressure and the residual oil was subjected to column chromatography on silica gel (5 g. elution with hexaneethyl acetate, 2:1 v/v, R$_f$0.10) to afford 48.6 mg (70%) of the diol. The enantiomeric excess of the diol was determined by HPLC analysis of the derived bis-acetate (Pirkle 1A column using 0.5% isopropanol/hexane mixture as eluant. Retention times are: t$_1$=17.1 minutes; t$_2$=18.1 minutes) to be 73%.

EXAMPLE 14 General Method for the Asymmetric Dihydroxylation of trans-Stilbene Using A Polymeric Alkaloid Ligand To a magnetically stirred suspension of the alkaloid copolymer (such as polymers 2–4, Table 1; 0.25 eq based on alkaloid incorporated), NMO (1.5 eq), and tetraethylammonium acetate tetrahydrate (1.0 eq) in acetone-water (10/1, v/v) a solution of OsO$_4$ (0.01 eq) in either toluene or acetonitrile was added. After stirring for 10–30 minutes, trans-stilbene (1.0 eq) was added and the reaction mixture was stirred for the given time and monitored by silica gel TLC (hexane-EtOAc 2/1, v/v). The concentration of olefin in the reaction mixture was 0.3–0.4M. After the reaction was complete, the mixture was diluted with acetone, water, hexane or ether and centrifuged or filtered to separate the polymer from the reaction mixture. The supernatant was then worked up as described by Jacobsen et al., *J. Am. Chem. Soc.*, 110:1968 (1988).

EXAMPLE 15 Asymmetric Dihydroxylation of trans-Stilbene Using A Polymer-Bound Alkaloid Ligand and Potassium Ferricyanaide To a well-stirred mixture of the alkaloid polymer (0.05 mmol, based on alkaloid incorporated), potassium ferricyanide (0.198 g, 0.6 mmol) and potassium carbonate (0.83 g, 0.6 mmol) in tert-butanol (1.5 mL) and water (1.5 mL), was added OsO$_4$ solution (0.0025 mmol) in acetonitrile. After stirring for 10 min, trans-stilbene (36 mg. 0.2 mmol) was added and the mixture was stirred for the given time and monitored by silica gel TLC. When the reaction was complete, water (3.0 mL) was added and the mixture was filtered. The filtrate was extracted with dichloromethane (5 mL×2). the organic layer was stirred for 1 h with excess sodium metabisulfite and sodium sulfate. This suspension was filtered and the filtrate was concentrated to provide crude diol, which was purified on a silica gel column.

EXAMPLE 16 Asymmetric Dihydroxylation of Olefins in the Presence of Potassium Ferricyanide The general procedure for asymmetric dihydroxylation of olefins using potassium ferricyanide:

To a well-stirred mixture of 0.465 g (1 mmol, 0.5 equiv=0.033M in ligand) dihydroquinidine p-cholorobenzoate (Aldrich, 98%), 1.980 g (6 mmol, 3.0 equiv) potassium ferricyanide, 0.830g (6 mmol, 3.0 equiv) potassium carbonate, and 0.5 mL of a 0.05M tert-butyl alcohol solution of osmium tetroxide (0.025 mmol, 0.0125 equiv) in 30 mL of a tert-butyl alcohol-water mixture (1:1. v/v) at room temperature, olefin (2 mmol) was added at at once. The reaction mixture was stirred for 24 h at room temperature. Solid sodium sulfite (Na₂SO₃, 1.5 g) was added, and the mixture was stirred for an additional hour. The solution obtained was concentrated to dryness under reduced pressure, and the residue was extracted with three portions of ether. The combined extracts were dried (Na₂SO₄) and evaporated. The residue was purified by column chromatography (silica gel, dichloromethane-ether).

EXAMPLE 17 Preparation of 9-O-Phenyldihydroquinidine

To a suspension of dihydroquinidine (4.0 g) in THF (40 mL) was added η-BuLi (2.5M solution in hexane, 4.95 mL) at 0° C. The ice bath was removed and the reaction mixture stood at room temperature for 10 minutes. To the resulting yellow solution, solid cuprous chloride (1.2 g) was added. After stirring for 30 minutes, pyridine (30 mL) and HMPA (1 mL) were added. After stirring for 5 minutes, phenyl iodide (1.37 mL) was added and the mixture was stirred at reflux for 36 h. To the resulting mixture, aqNH₄OH was added and the mixture was extracted with ethyl ether. The extract was dried over MgSO₄. The solvent was evaporated under reduced pressure, and the residue was subjected to column chromatography on silica gel (100 g. elution with ethyl acetate-ethanol, 9:1 v/v, Rf 0.23) to afford 1.77 g(y. 36%) of 9-O-phenyldihydroquinidine. ¹H NMR (CDCl₃) δ 8/68 (1H, d, J=4.5 Hz), 8.08 (1 H, d, J =9 Hz), 7.3–7.5 (3H, m), 7.17 (2H, t, J=8 Hz), 6.89 (1H, t, J=8 Hz), 6.78 (2H, d, J=8 Hz), 6.02 (1H, d, J =3 Hz), 4.00 (3H, s), 2.7–3.3 (5H, m), 2.2 2.4 (1H, m), 1.4–1.9 (6H, m), 1.1–1.3 (1H, m), 0.97 (3H, t, J=7 Hz).

EXAMPLE 18 Asymmetric Dihydroxyration of Trans-3-Hexene Using 9-O-Phenyldihydroquinigine and Potassium Ferricyanide To a well stirred mixture of 46 mg of 9-O-phenyldihydroquinidine, 396 mg of potassium ferricyanide, 166 mg of potassium cabonate and 8 μL of a 0.63M toluene solution of osmium tetroxide in 6 mL of t-butyl alcohol-water (1:1. v/v) at room temperature was added 50 μL of trans-3-hexene all at once. The reaction mixture was stirred for 20 h at room temperature. Solid sodium sulfite was added and the mixture was stirred for 3 h. The solid was removed by filtration and the filtrate was extracted with ethyl ether. The extract was dried over mgSO₄. The solvent was evaporated under reduced pressure, and the residue was subjected to column chromatography on silica gel (elution with hexane-ethyl acetate, 2:1 v/v) to afford 40.5 mg (y. 85%) of the diol. The enantiomeric excess of the diol was determined by GLC analysis of the derived bis-Mosher ester (5% phenylmethylsilicone, 0.25 m film, 0.317 mm diameter. 29 m long. Retention times are t₁=15.6 min; t₂=16.0 min ) to be 83%.

EXAMPLE 19 Asymmetric Oxyamination of Trans-Stilbene Using N-Chloro-N-Sodio-t-Butylcarbamate To a well-stirred mixture of 81 mg trans-stilbene 122 mg of N-chloro-N-sodio-t-butylcarbamate, 95 mg of murcuric chloride, 209 mg of dihydroquinidine p-chlorobenzoate and 370 μL of water acetonitrile (5 mL) was added 9 μL of a 0.5M toluene solution of osmium tetroxide. The mixture was stirred at room temperature overnight. Solid sodium sulfite and water were added, and the mixture was stirred at 60° C. for 1 hour. The mixture was extracted with dichloromethane and the extract was dried over MgSO₄. The solvent was evaporated under reduced pressure, and the residue was subjected to column chromatography on silica gel (elution with hexane ethyl acetate, 4:1 v/v, Rf 0.13) to afford 131 mg (y. 93%) of the aminoalcohol. The enantiomeric excess of the aminoalcohol was determined by HPLC analysis (Pirkle Covalent Phenyl Glycine column using 10% isopropanol/hexane mixture as eluant. Retention times are: t₁=12.7 min; t₂=15.2 min.) to be 65%. ¹H NMR (CDCl₃) δ7.1.7.4 (10 H, m), 5.3–5.4 (1H, m). 4.95 (1H, d, J=3.5 Hz). 4.8–5.0 (1H, m), 2.6–2.7 (1H, m), 1.34 (9H, ).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. A method of osmium-catalyzed asymmetric addition to an olefin, comprising combining the olefin, a polymeric cinchona alkaloid chiral ligand or derivative thereof, an organic solvent, water, an oxidant and an osmium-containing catalyst, and maintaining the combination under conditions appropriate for asymmetric addition to the olefin to occur.

2. A method of claim 1 wherein the oxidant is a combination of potassium ferricyanide and a strong base, wherein the amount of strong base is at least double the amount of olefin, and the organic solvent is tert-butyl alcohol.

3. A method of claim 2 wherein the strong base is potassium carbonate.

4. A method of claim 1 wherein the polymeric cinchona alkaloid chiral ligand or derivative thereof is selected from the group consisting of an acrylonitrile co-polymer of 9-(4-chlorobenoyloxy)-quinidine, an acrylonitrile co-polymer of 11-[(2-acryloyloxy)ethyl-sulfinyl]-9-(4-chlorobenoyloxy)-10,11-dihydroquinidine, an acrylonitrile co-polymer of 11-[(2-acryloyloxy)ethyl-sulfonyl]-9-(N,N-dimethylcarbamoyl)-10,11-dehydroquinidine and an acrylonitrile co-polymer of 9-(10-undecanoyl)-10,11-dihydroquinidine.

5. A method of osmium-catalyzed asymmetric dihydroxylation of an olefin, comprising combining the olefin, a selected polymeric cinchona alkaloid chiral or derivative thereof ligand, organic solvent, water, an amine oxide and an osmium-containing compound, the osmium-containing compound added in sufficient quantity to provide a catalytic amount of osmium, under conditions appropriate for asymmetric dihydroxylation to occur.

6. A method of claim 5, wherein the the amine oxide is N-methylmorpholine N-oxide and the osmium-containing compound is osmium tetroxide.

7. A method of claim 6 wherein the polymeric cinchona alkaloid chiral ligand or derivative thereof is selected from the group consisting of an acrylonitrile co-polymer of 9-(4-chlorobenoyloxy)-quinidine, an acrylonitrile co-polymer of 11-[(2-acryloyloxy)ethyl-sulfinyl]-9-(4-chlorobenoyloxy)-10,11-dihydroquinidine, an acrylonitrile co-polymer of 11-[(2-acryloyloxy)ethyl-sulfonyl]-9-(N,N-dimethylcarbamoyl)-10,11-dihydroquinidine and an acrylonitrile co-polymer of 9-(10-undecanoyl)-10,11-dihydroquinidine.

8. A method of claim 5 wherein a combination of potassium ferricyanide and a strong base is added in lieu of the amine oxide, wherein the amount of strong base is at least double the amount of olefin.

9. A method of claim 8 wherein the strong base is potassium carbonate.

10. An osmium-catalyzed method of asymmetric dihydroxylation of an olefin, comprising the steps of:
   a) combining the olefin, a polymeric cinchona alkaloid chiral ligand or a derivative thereof, an organic solvent, water and a selected oxidant;
   b) adding an osmium-containing catalyst to the combination formed in (a); and
   c) maintaining the resulting combination produced in (b) under conditions appropriate for asymmetric dihydroxylation of the olefin to occur.

11. A method of claim 10, wherein the polymeric cinchona alkaloid chiral ligand derivative is a dihydroquinidine derivative or a dihydroquinine derivative, the oxidant is N-methyl morpholine N-oxide and the osmium-containing compound is osmium tetroxide.

12. A method of claim 11 wherein the polymeric cinchona alkaloid chiral ligand derivative is selected from the group consisting of an acrylonitrile co-polymer of 9-(4-chlorobenoyloxy)quinidine, an acrylonitrile co-polymer of 11-[(2-acryloyloxy)ethyl-sulfinyl]-9-(4-chlorobenoyloxy)-10,11-dihydroquinidine, an acrylonitrile co-polymer of 11-[(2-acryloyloxy)-ethylsulfonyl]-9-(N,N-dimethylcarbamoyl)-10,11-dihydroquinidine and an acrylonitrile co-polymer of 9-(10-undecanoyl)-10,11-dihydroquinidine.

13. A method of claim 10 wherein the oxidant is a combination of potassium ferricyanide and potassium carbonate δ, and the organic solvent is tert-butyl alcohol.

14. An osmium-catalyzed method of producing an asymmetrically dihydroxylated olefin, comprising:
   a) combining 1) the olefin, 2) a cinchona alkaloid derivative, 3) an organic solvent, 4) a strong base and 5) potassium ferricyanide, to form a reaction mixture, wherein the amount of strong base is at least double the amount of olefin, the cinchona alkaloid present in a concentration of from approximately 0.01M to approximately 2.0M;
   b) adding osmium tetroxide in a catalytic quantity to the reaction mixture; and
   c) maintaining the product of step (b) under conditions appropriate for dihydroxylation of the olefin to occur.

15. A method of claim 14 wherein the osmium tetroxide reacts with the cinchona alkaloid chiral ligand to form a cinchona alkaloid-osmium complex.

16. A method of claim 14 wherein the strong base is potassium carbonate.

17. A method of claim 14 wherein the organic solvent is tert-butyl alcohol.

18. An osmium-catalyzed method of asymmetric dihydroxylation of an olefin, comprising the steps of:
   a. combining a cinchona alkaloid chiral ligand or a derivative thereof immobilized on a polymer, an organic solvent, water, a strong base and potassium, wherein the amount of strong base is at least double the amount of olefin ferricyanide;
   b. adding an osmium containing catalyst to the combination formed in (a); and
   c. adding the olefin slowly to the combination formed in (b) under conditions appropriate for asymmetric dihydroxylation of the olefin to occur.

19. A method of claim 18, wherein the base is potassium carbonate, the organic solvent is tert-butyl alcohol and the osmium containing compound is osmium tetroxide.

20. A method of claim 18 wherein the cinchona alkaloid chiral ligand is a polymeric alkaloid or alkaloid derivative which is selected from the group consisting of an acrylonitrile co-polymer of 9-(4-chlorobenoyloxy)quinidine, an acrylonitrile co-polymer of 11-[(2-acryloyloxy)ethyl-sulfinyl]-9-(4-chlorobenoyloxy)-10,11-dihydroquinidine, an acrylonitrile co-polymer of 11-[(2-acryloyloxy)-ethylsulfonyl]-9-(N,N-dimethylcarbamoyl)-10,11-dihydroquinidine and an acrylonitrile co-polymer of 9-(10-undecanoyl)-10,11-dihydroquinidine.

21. An osmium-catalyzed method of asymmetric dihydroxylation of an olefin, comprising the steps of:
   a. combining a polymeric cinchona alkaloid chiral ligand or a derivative thereof, an organic solvent, a strong base and potassium ferricyanide, wherein the amount of strong base is at least double the amount of olefin;
   b. adding an osmium containing catalyst to the combination formed in (a); and
   c. adding the olefin slowly to the combination formed in (b) under conditions appropriate for asymmetric dihydroxylation of the olefin to occur.

22. A method of claim 21, wherein the polymeric cinchona alkaloid chiral ligand is an aryl ether of a cinchona alkaloid, and the osmium-containing compound is osmium tetroxide.

23. A method of claim 21 wherein the polymeric cinchona alkaloid chiral ligand derivative is selected from the group consisting of an acrylonitrile co-polymer of 9-(4-chlorobenoyloxy)quinidine, an acrylonitrile co-polymer of 11-[(2-acryloyloxy)-ethyl-sulfinyl]-9-(4-chlorobenoyloxy)-10,11-dihydroquinidine, an acrylonitrile co-polymer of 11-[(2-acryloyloxy)ethylsulfonyl]-9-(N,N-dimethylcarbamoyl)-10,11-dihydroquinidine and an acrylonitrile co-polymer of 9-(10-undecanoyl)-10,11-dihydroquinidine.

* * * * *

UNITED STATES PATENT AND TRADEMARK OFFICE
CERTIFICATE OF CORRECTION

PATENT NO. : 5,126,494
DATED : June 30, 1992
INVENTOR(S) : Declan Gilheany, Byeong Moon Kim, Hoi-Lon Kwong, K. Barry Sharpless and Tomoyuki Shibata It is certified that error appears in the above-indentified patent and that said Letters Patent is hereby corrected as shown below:

Column 38:

Claim 5, line 49 after "chiral", insert --ligand--.

Claim 5, line 50, remove "ligand".

Column 40:

Claim 18, line 8, after "potassium", insert --Ferricyanide--.

Claim 18, line 9, remove "ferricyanide".

Signed and Sealed this

Twelfth Day of October, 1993

Attest:

BRUCE LEHMAN

Attesting Officer    Commissioner of Patents and Trademarks